United States Patent
Papas

(10) Patent No.: US 12,115,332 B2
(45) Date of Patent: Oct. 15, 2024

(54) METHODS AND SYSTEMS FOR ENCAPSULATION DEVICES FOR HOUSING CELLS AND AGENTS

(71) Applicants: Arizona Board of Regents on Behalf of the University of Arizona, Tucson, AZ (US); Procyon Technologies LLC, Tucson, AZ (US)

(72) Inventor: Klearchos Papas, Tucson, AZ (US)

(73) Assignees: Arizona Board of Regents on Behalf of the University of Arizona, Tuscon, AZ (US); Procyon Technologies LLC, Tucson, AZ (US)

( * ) Notice: Subject to any disclaimer, the term of this patent is extended or adjusted under 35 U.S.C. 154(b) by 160 days.

(21) Appl. No.: 17/516,179

(22) Filed: Nov. 1, 2021

(65) Prior Publication Data

US 2022/0134074 A1    May 5, 2022

Related U.S. Application Data

(60) Provisional application No. 63/108,017, filed on Oct. 30, 2020.

(51) Int. Cl.
*A61M 37/00* (2006.01)
*A61F 2/02* (2006.01)
(Continued)

(52) U.S. Cl.
CPC ......... *A61M 37/0069* (2013.01); *A61F 2/022* (2013.01); *A61L 27/52* (2013.01);
(Continued)

(58) Field of Classification Search
CPC .......... A61M 37/0069; A61M 2202/03; A61M 2205/04; A61F 2/022; A61L 27/52; A61L 27/54; A61L 2300/62
See application file for complete search history.

(56) References Cited

U.S. PATENT DOCUMENTS 4,902,476 A * 2/1990 Gordon ................. B01D 63/02
                                                  165/184
5,169,390 A   12/1992 Athayde et al.
(Continued)

FOREIGN PATENT DOCUMENTS

CA    3042709     8/2018
CN    101123984   2/2008
(Continued)

OTHER PUBLICATIONS

"Membrane Basics," PermSelect—Silicone Gas Exchange Membranes, 2021, retrieved from https://www.permselect.com/membranes, 9 pages.
(Continued)

*Primary Examiner* — Susan S Su
*Assistant Examiner* — Ted Yang
(74) *Attorney, Agent, or Firm* — Sheridan Ross P.C.

(57) ABSTRACT

Embodiments of the present disclosure relate to encapsulation devices, systems and methods of use. In some embodiments, encapsulation devices for housing cells and providing various therapeutic benefits to a patient or host are described. Encapsulation devices include, for example, a matrix or scaffold within a cell-receiving area or void. Encapsulation devices may include channels that are operable to convey fluid to internal areas of devices without restricting vascularization.

12 Claims, 16 Drawing Sheets

(51) Int. Cl.
  *A61L 27/52* (2006.01)
  *A61L 27/54* (2006.01)
(52) U.S. Cl.
  CPC ............ *A61L 27/54* (2013.01); *A61L 2300/62* (2013.01); *A61M 2202/03* (2013.01); *A61M 2205/04* (2013.01)

(56) References Cited

U.S. PATENT DOCUMENTS

| | | | |
|---|---|---|---|
| 5,324,518 A * | 6/1994 | Orth | A61M 39/0208 604/93.01 |
| 5,368,028 A * | 11/1994 | Palti | A61B 5/0031 604/522 |
| 5,595,621 A | 1/1997 | Light et al. | |
| 5,626,561 A | 5/1997 | Butler et al. | |
| 5,713,888 A | 2/1998 | Brauker et al. | |
| 5,741,330 A | 4/1998 | Brauker et al. | |
| 5,814,405 A | 9/1998 | Branca et al. | |
| 5,837,234 A | 11/1998 | Yapel et al. | |
| 5,843,069 A | 12/1998 | Butler et al. | |
| 5,882,354 A | 3/1999 | Brauker et al. | |
| 5,980,889 A | 11/1999 | Butler et al. | |
| 6,060,640 A * | 5/2000 | Pauley | A61F 2/022 623/1.41 |
| 6,143,293 A | 11/2000 | Calvert et al. | |
| 6,156,305 A | 12/2000 | Brauker et al. | |
| 6,197,575 B1 | 3/2001 | Griffith et al. | |
| 6,562,616 B1 | 5/2003 | Toner et al. | |
| 7,659,219 B2 | 2/2010 | Biran et al. | |
| 7,892,222 B2 * | 2/2011 | Vardi | A61F 2/022 604/93.01 |
| 8,278,106 B2 | 10/2012 | Martinson et al. | |
| 8,518,123 B2 | 8/2013 | Jensen et al. | |
| 8,647,861 B2 | 2/2014 | Ingber et al. | |
| 9,433,557 B2 * | 9/2016 | Green | A61J 1/20 |
| 10,695,379 B2 | 6/2020 | Greenwood et al. | |
| 11,033,666 B2 | 6/2021 | Ferrante et al. | |
| 2003/0054544 A1 | 3/2003 | Gruenberg | |
| 2003/0087427 A1 * | 5/2003 | Colton | A61K 33/00 435/289.1 |
| 2003/0129736 A1 | 7/2003 | Mitrani | |
| 2004/0010320 A1 | 1/2004 | Huckle et al. | |
| 2004/0024342 A1 | 2/2004 | Weitzel et al. | |
| 2004/0133188 A1 * | 7/2004 | Vardi | A61F 2/022 424/93.1 |
| 2004/0166141 A1 | 8/2004 | Cerami et al. | |
| 2004/0197374 A1 | 10/2004 | Ghabrial et al. | |
| 2005/0136092 A1 * | 6/2005 | Rotem | A61P 25/00 424/195.17 |
| 2005/0221485 A1 | 10/2005 | Bader | |
| 2005/0267440 A1 | 12/2005 | Herman et al. | |
| 2006/0013835 A1 | 1/2006 | Anderson et al. | |
| 2006/0019333 A1 * | 1/2006 | Rodgers | B01D 61/002 435/41 |
| 2007/0061015 A1 | 3/2007 | Biris et al. | |
| 2007/0066138 A1 | 3/2007 | Ferrari et al. | |
| 2008/0021436 A1 | 1/2008 | Wolpert et al. | |
| 2009/0074832 A1 | 3/2009 | Zussman et al. | |
| 2009/0110669 A1 * | 4/2009 | Schneiderman | C12N 5/0691 435/395 |
| 2010/0082114 A1 * | 4/2010 | Gingras | A61F 2/02 623/23.76 |
| 2010/0124564 A1 | 5/2010 | Martinson et al. | |
| 2010/0130916 A1 * | 5/2010 | Stern | A61F 2/022 604/23 |
| 2010/0160760 A1 | 6/2010 | Shults et al. | |
| 2010/0172952 A1 * | 7/2010 | Srouji | A61L 27/56 424/602 |
| 2010/0196439 A1 * | 8/2010 | Beck | A61L 27/3616 424/424 |
| 2010/0228110 A1 * | 9/2010 | Tsoukalis | A61B 5/686 600/347 |
| 2010/0240117 A1 | 9/2010 | Ying et al. | |
| 2010/0255059 A1 | 10/2010 | Marquez et al. | |
| 2011/0054589 A1 | 3/2011 | Bashiri et al. | |
| 2011/0092949 A1 | 4/2011 | Wang | |
| 2012/0041355 A1 | 2/2012 | Edman et al. | |
| 2012/0245705 A1 | 9/2012 | Hasilo et al. | |
| 2013/0289540 A1 | 10/2013 | Zeltser et al. | |
| 2013/0344131 A1 | 12/2013 | Lo et al. | |
| 2014/0014226 A1 | 1/2014 | Baetge et al. | |
| 2014/0039383 A1 | 2/2014 | Dobbles et al. | |
| 2014/0051162 A1 | 2/2014 | Nankervis | |
| 2014/0052095 A1 | 2/2014 | Dobbles et al. | |
| 2014/0088347 A1 | 3/2014 | Frigstad et al. | |
| 2014/0236078 A1 * | 8/2014 | Dalton | A61M 5/14276 604/151 |
| 2014/0257515 A1 * | 9/2014 | So | A61P 3/10 623/23.64 |
| 2014/0308315 A1 | 10/2014 | Knezevich et al. | |
| 2015/0112247 A1 | 4/2015 | Papas et al. | |
| 2015/0129497 A1 | 5/2015 | Humes et al. | |
| 2015/0273200 A1 | 10/2015 | Rotem et al. | |
| 2015/0320836 A1 | 11/2015 | Itkin-Ansari et al. | |
| 2015/0359472 A1 | 12/2015 | Botvinnick et al. | |
| 2016/0022180 A1 | 1/2016 | Joseph et al. | |
| 2016/0038207 A1 | 2/2016 | Wei et al. | |
| 2016/0082236 A1 | 3/2016 | Botvinick et al. | |
| 2016/0123848 A1 | 5/2016 | Griffin et al. | |
| 2016/0184569 A1 | 6/2016 | Bouche et al. | |
| 2017/0072074 A1 * | 3/2017 | Gladnikoff | A61K 49/0045 |
| 2017/0173262 A1 * | 6/2017 | Veltz | G16H 20/17 |
| 2018/0000395 A1 | 1/2018 | Lucisano et al. | |
| 2018/0126134 A1 * | 5/2018 | Cully | A61K 9/0092 |
| 2018/0263238 A1 | 9/2018 | Flanagan et al. | |
| 2018/0298343 A1 | 10/2018 | Sivakumaran | |
| 2018/0318566 A1 | 11/2018 | Ferrante et al. | |
| 2018/0344665 A1 * | 12/2018 | Isenburg | A61K 36/185 |
| 2019/0076840 A1 | 3/2019 | Gottardi et al. | |
| 2019/0136176 A1 | 5/2019 | Kawachi et al. | |
| 2019/0211294 A1 | 7/2019 | Karnieli | |
| 2019/0224377 A1 | 7/2019 | Papas | |
| 2019/0328289 A1 | 10/2019 | Papas | |
| 2019/0336267 A1 * | 11/2019 | Tempelman | A61F 2/022 |
| 2020/0054257 A1 | 2/2020 | Papas | |
| 2020/0063085 A1 | 2/2020 | Papas | |
| 2020/0281709 A1 | 9/2020 | Papas | |
| 2021/0386333 A1 | 12/2021 | Papas | |
| 2021/0401564 A1 | 12/2021 | Neuenfeldt et al. | |

FOREIGN PATENT DOCUMENTS

| | | | |
|---|---|---|---|
| CN | 201337642 | 11/2009 | |
| CN | 102012390 | 4/2011 | |
| CN | 203915611 | 11/2014 | |
| CN | 105163688 | 12/2015 | |
| CN | 105792775 | 7/2016 | |
| DE | 8909058 | 9/1989 | |
| EP | 0344314 | 12/1989 | |
| EP | 1351623 | 10/2003 | |
| EP | 2508212 | 10/2012 | |
| JP | H06-205665 | 7/1994 | |
| JP | 2004-530431 | 10/2004 | |
| JP | 2014-514942 | 6/2014 | |
| KR | 10-2012-0091008 | 8/2012 | |
| KR | 10-2014-0023252 | 2/2014 | |
| KR | 10-2016-0094391 | 8/2016 | |
| WO | WO 91/00119 | 1/1991 | |
| WO | WO-9632076 A1 * | 10/1996 | A61F 2/022 |
| WO | WO 01/12158 | 2/2001 | |
| WO | WO 02/100335 | 12/2002 | |
| WO | WO 2006/106506 | 10/2006 | |
| WO | WO 2008/100559 | 8/2008 | |
| WO | WO 2010/061387 | 6/2010 | |
| WO | WO 2012/136701 | 10/2012 | |
| WO | WO 2014/173441 | 10/2014 | |
| WO | WO 2015/145264 | 10/2015 | |
| WO | WO 2018/067813 | 4/2018 | |
| WO | WO 2018/085714 | 5/2018 | |
| WO | WO 2018/089397 | 5/2018 | |
| WO | WO 2018/102077 | 6/2018 | |

(56) References Cited

FOREIGN PATENT DOCUMENTS

| WO | WO 2018/144098 | 8/2018 |
|---|---|---|
| WO | WO 2018/144099 | 8/2018 |
| WO | WO 2022/094380 | 5/2022 |

OTHER PUBLICATIONS

Carlsson et al., "Transplantation of macroencapsulated human islets within the bioartificial pancreas BAir to patients with type 1 diabetes mellitus," American Journal of Transplantation, vol. 18, 2018, pp. 1735-1744.
Geller et al., "Use of an Immunoisolation Device for Cell Transplantation and Tumor Immunotherapy." Annals New York Academy of Science, Date Unnknown, 14 pages.
Gholipourmalekabadi et al., "Oxygen-Generatin Biomaterials: A New, Viable Paradigm for Tissue Engineering?" Trends in Biotechnology, vol. 34, No. 12, Dec. 2016, pp. 1010-1021.
Knoepiler, "ViaCyte CEO Paul Laikind Interview: Trial Update, Melton's Concerns, & Future," The Niche, Mar. 2, 2015, retrieved from https://ipscell.com/2015/03/viacyte, 6 pages.
Krishnan et al., "Islet And Stem Cell Encapsulation for Clinical Transplantation," Review of Diabetic Studies, vol. 11, No. 1, 2014, pp. 84-101.
Lathuiliere et al., "Encapsulated Cellular Implants for Recombinant Protein Delivery and Therapeutic Modulation of the Immune System," International Journal of Molecular Sciences, vol. 16, 2015, pp. 10578-10600.
Lee et al., "Cytokines in Cancer Immunotherapy," Cancers, vol. 3, 2011, pp. 3856-3893.
Makadia et al., "Poly Lactic-co-Glycolic Acid (PLGA) as Biodegradable Controlled Drug Delivery Carrier," Polymers (Basel), vol. 3, No. 3, Sep. 1, 2011, pp. 1377-1397.
Manickavasagam et al., "Critical Assessment of Implantable Drug Delivery Devices in Glaucoma Management," Jounral of Drug Delivery, vol. 2013, No. 895013, Jul. 2013, 12 pages.
Wang et al., "Overcoming foreign-body reaction through nanotopography: Biocompatibility and Immunoisolation properties of a nanofibrous membrane," Biomaterials, vol. 102, Sep. 30, 2016, pp. 249-258.
International Search Report and Written Opinion for International (PCT) Patent Application No. PCT/US2017/060036, dated Feb. 16, 2018, 14 pages.
Official Action for Australia Patent Application No. 2017355528, dated Aug. 20, 2020, 5 pages.
Official Action for Australia Patent Application No. 2017355528, dated Nov. 16, 2020, 4 pages.
Notice of Acceptance for Australia Patent Application No. 2017355528, dated Mar. 22, 2021, 4 pages.
Official Action for Australia Patent Application No. 2021204321, dated Jun. 6, 2022, 3 pages.
Official Action for China Patent Application No. 201780081318.9, dated Feb. 1, 2021, 8 pages.
Official Action for China Patent Application No. 201780081318.9, dated Sep. 1, 2021, 12 pages.
Official Action for China Patent Application No. 201780081318.9, dated Apr. 7, 2022, 22 pages.
Extended European Search Report for Europe Patent Application No. 17866485.0, dated Apr. 25, 2020, 9 pages.
Official Action for Korea Patent Application No. 10-2019-7015936, dated Feb. 22, 2022, 11 pages.
International Search Report and Written Opinion for International (PCT) Patent Application No. PCT/US2017/060034, dated Jul. 12, 2018, 9 pages.
Official Action for Australia Patent Application No. 2017396753, dated Jul. 23, 2020, 4 pages.
Official Action for Australia Patent Application No. 2017396753, dated Jan. 27, 2021, 5 pages.
Notice of Acceptance for Australia Patent Application No. 2017396753, dated Apr. 20, 2021, 4 pages.
Official Action for Australia Patent Application No. 202106840, dated Jun. 6, 2022, 3 pages.
Official Action for China Patent Application No. 201780081104.1, dated Apr. 2, 2021, 10 pages.
Official Action for China Patent Application No. 201780081104.1, dated Dec. 2, 2021, 11 pages.
Extended European Search Report for European Patent Application No. 17895433.5, dated Apr. 17, 2020, 7 pages.
Official Action for Korea Patent Application No. 10-2019-7015935, dated Feb. 8, 2022, 9 pages.
International Search Report and Written Opinion for International (PCT) Patent Application No. PCT/US2017/060014, dated Jul. 10, 2018, 14 pages.
Official Action for Australian Patent Application No. 2017396754, dated Nov. 12, 2020, 7 pages.
Notice of Allowance for Australian Patent Application No. 2017396754, dated Jul. 21, 2021, 4 pages.
Official Action for China Patent Application No. 201780081103.7, dated Jan. 11, 2021, 11 pages.
Official Action for China Patent Application No. 201780081103.7, dated Nov. 1, 2021, 11 pages.
Notice of Allowance for China Patent Application No. 201780081103.7, dated Mar. 23, 2022, 2 pages.
Extended European Search Report for Europe Patent Application No. 17894862.6, dated May 20, 2020, 4 pages.
Official Action for Korea Patent Application No. 10-2019-7015937, dated Jan. 12, 2022, 14 pages.
Notice of Allowance for Korea Patent Application No. 10-2019-7015937, dated May 20, 2022, 6 pages.
International Search Report and Written Opinion for International (PCT) Patent Application No. PCT/US2017/060043, dated Jun. 14, 2018, 9 pages.
Official Action for Australi Patent Application No. 2017366791, dated Jun. 22, 2020, 4 pages.
Notice of Allowance for Australia Patent Application No. 2017366791, dated Jan. 8, 2021, 4 pages.
Official Action for China Patent Application No. 201780081105.6, dated Aug. 9, 2021, 12 pages.
Official Action for China Patent Application No. 201780081105.6, dated Mar. 24, 2022, 12 pages.
Extended European Search Report for Europe Patent Application No. 17875181.4, dated Apr. 28, 2020, 4 pages.
Official Action for Korea Patent Application No. 10-2019-7015938, dated Sep. 30, 2021, 5 pages.
International Search Report and Written Opinion for International (PCT) Patent Application No. PCT/US2019/052728, dated Dec. 13, 2019, 10 pages.
International Preliminary Report on Patentability for International (PCT) Application No. PCT/US2019/052728, dated Apr. 1, 2021, 9 pages.
Official Action for Australia Patent Application No. 2019346547, dated Feb. 9, 2022, 4 pages.
Official Action for Canada patent Application No. 3114197, dated Jun. 6, 2022, 6 pages.
Partial Supplementary European Search Report for Europe Patent Application No. 19867716.3, dated May 23, 2022, 13 pages.
Official Action for India Patent Application No. 202117012735, dated Feb. 11, 2022, 5 pages.
Invitation to Pay additional Fees for International (PCT) Patent Application No. PCT/US2021/057526, dated Jan. 5, 2022, 3 pages.
International Search Report and Written Opinion for International (PCT) Patent Application No. PCT/US2021/057526, dated Mar. 2, 2022, 16 pages.
Official Action for U.S. Appl. No. 16/647,338, dated Jun. 16, 2022, 10 pages.
Official Action for U.S. Appl. No. 16/347,388, dated May 11, 2021, 10 pages.
Official Action for U.S. Appl. No. 16/347,388, dated Oct. 4, 2021, 10 pages.
Notice of Allowance for U.S. Appl. No. 16/347,388, dated May 12, 2022, 10 pages.
Corrected Notice of Allowance for U.S. Appl. No. 16/347,388, dated May 20, 2022, 6 pages.

(56) References Cited

OTHER PUBLICATIONS

Official Action for U.S. Appl. No. 16/347,147, dated Apr. 8, 2021, 8 pages. Restriction Requirement.
Official Action for U.S. Appl. No. 16/347,147, dated Jul. 2, 2021, 12 pages.
Official Action for U.S. Appl. No. 16/347,147, dated Nov. 12, 2021, 11 pages.
Official Action for U.S. Appl. No. 16/347,147, dated Jun. 2, 2022, 14 pages.
Official Action for U.S. Appl. No. 16/347,160, dated Dec. 28, 2020, 15 pages.
Official Action for U.S. Appl. No. 16/347,160, dated Nov. 29, 2021, 14 pages.
Official Action for U.S. Appl. No. 17/387,595, dated Nov. 10, 2021, 15 pages.
Official Action for U.S. Appl. No. 17/387,595, dated Mar. 28, 2022, 18 pages.
Suszynski et al., "Assessment of Tissue-Engineered Islet Graft Viability by Fluorine Magnetic Resonance Spectroscopy," Transplant Proc., vol. 43, No. 9, Nov. 2011, pp. 3221-3225.
Official Action for Singapore Patent Application No. 11201905391W, dated Apr. 28, 2023, 4 pages.
Official Action for Australia Patent Application No. 2021206840, dated May 1, 2023, 4 pages.
Official Action for Australia Patent Application No. 2021206840, dated May 30, 2023, 3 pages.
Notice of Allowance for Australia Patent Application No. 202106840, dated Jun. 8, 2023, 4 pages.
Official Action for Korea Patent Application No. 10-2022-7037085, dated Jun. 20, 2023, 9 pages.
Official Action for Korea Patent Application No. 10-2022-7037086, dated Jun. 15, 2023, 6 pages.
Official Action (with English summary) for China Patent Application No. 201780081105.6, dated Apr. 18, 2023, 8 pages.
Official Action for Singapore Patent Application No. 11201905390Q, dated Apr. 28, 2023, 3 pages.
Notice of Allowance for Canada Patent Application No. 3114197, dated Apr. 17, 2023, 1 page.
Official Action (with English translation) for Korea Patent Application No. 10-2021-7012313, dated Mar. 3, 2023, 17 pages.
Official Action for Taiwan Patent Application No. 108134435, dated Jul. 18, 2023, 11 pages.
International Preliminary Report on Patentability for International (PCT) Application No. PCT/US2021/057526, dated May 11, 2023, 9 pages.
Notice of Allowance for U.S. Appl. No. 16/647,338, dated Mar. 24, 2023, 7 pages.
Notice of Allowance for U.S. Appl. No. 16/347,147, dated Apr. 17, 2023, 7 pages.
Corrected Notice of Allowance for U.S. Appl. No. 16/347,147, dated Apr. 20, 2023, 2 pages.
Official Action for U.S. Appl. No. 17/387,595, dated Apr. 10, 2023, 29 pages.
Official Action for U.S. Appl. No. 17/876,302, dated Apr. 3, 2023, 19 pages.
Official Action for Korea Patent Application No. 10-2019-7015936, dated Jul. 25, 2022, 5 pages.
Official Action for China Patent Application No. 201780081104.1, dated Jun. 30, 2022, 27 pages.
Notice of Allowance for Korea Patent Application No. 10-2019-7015935, dated Jul. 25, 2022, 3 pages.
Notice of Allowance for Korea Patent Application No. 10-2019-7015937, dated Jul. 22, 2022, 3 pages.
Official Action for China Patent Application No. 201780081105.6, dated Sep. 29, 2022, 8 pages.
Official Action for Australia Patent Application No. 2019346547, dated Sep. 2, 2022, 4 pages.
Extended European Search Report for Europe Patent Application No. 19867716.3, dated Oct. 6, 2022, 12 pages.
Official Action (with English summary) for Japan Patent Application No. 2021-540389, dated Jun. 21, 2022, 7 pages.
Official Action for U.S. Appl. No. 16/347,160, dated Jul. 7, 2022, 14 pages.
Official Action for U.S. Appl. No. 17/876,302, dated Oct. 25, 2022, 22 pages.
Official Action (no English translation available) for Korea Patent Application No. 10-2022-7028922, dated Feb. 3, 2023, 5 pages.
Official Action (with English translation) for China Patent Application No. 201980062844.X, dated Aug. 12, 2023, 30 pages.
Lemons et al., "Biomaterials Science: An Introduction to Materials In Medicine," Elsevier Science, 2004, pp. 88-89, 629, & 642. [best available quality].
Intent to Grant (with English translation) for China Patent Application No. 201780081104.1, dated Oct. 19, 2022, 6 pages.
Communication Pursuant to Article 94(3) for Europe Patent Application No. 17894862.6, dated Feb. 1, 2023, 9 pages.
Communication pursuant to Article 94(3) for Europe Patent Application No. 17875181.4, dated Feb. 9, 2023, 6 pages.
Krishnan et al., "Cellular Immunoisolation for Islet Transplantation by a Novel Dual Porosity Electrospun Membrane," Transplantation Proceedings, vol. 43, No. 9, Nov. 2011, pp. 3256-3261.
Lemons et al., "Biomaterials Science: An Introduction to Materials In Medicine," Elsevier Science, 2004, Table of Contents and Preface only.
Official Action for Australia Patent Application No. 2021204321, dated Jan. 19, 2023, 4 pages.
Notice of Allowance (with English translation) for China Patent Application No. 201780081318.9, dated Oct. 19, 2022, 6 pages.
Communication Pursuant to Article 94(3) for Europe Patent Application No. 17866485.0, dated Dec. 28, 2022, 6 pages.
Official Action for Korea Patent Application No. 2019-7015936, dated Nov. 29, 2022, 3 pages.
Official Action for Australia Patent Application No. 2021206840, dated Jan. 17, 2023, 3 pages.
Communication Pursuant to Article 94(3) for Europe Patent Application No. 17895433.5, dated Jan. 2, 2023, 4 pages.
Official Action for Australia Patent Application No. 2021202373, dated Oct. 24, 2022, 7 pages.
Official Action for Australia Patent Application No. 2019346547, dated Jan. 13, 2023, 6 pages.
Official Action (with English summary) for Japan Patent Application No. 2021-540389, dated Jan. 17, 2023, 6 pages.
Official Action for U.S. Appl. No. 16/647,338, dated Dec. 15, 2022, 9 pages.
Official Action for U.S. Appl. No. 16/347,147, dated Jan. 10, 2023, 15 pages.
Official Action for U.S. Appl. No. 16/347,160, dated Dec. 19, 2022, 19 pages.
Official Action for U.S. Appl. No. 17/387,595, dated Dec. 19, 2022, 20 pages.

* cited by examiner

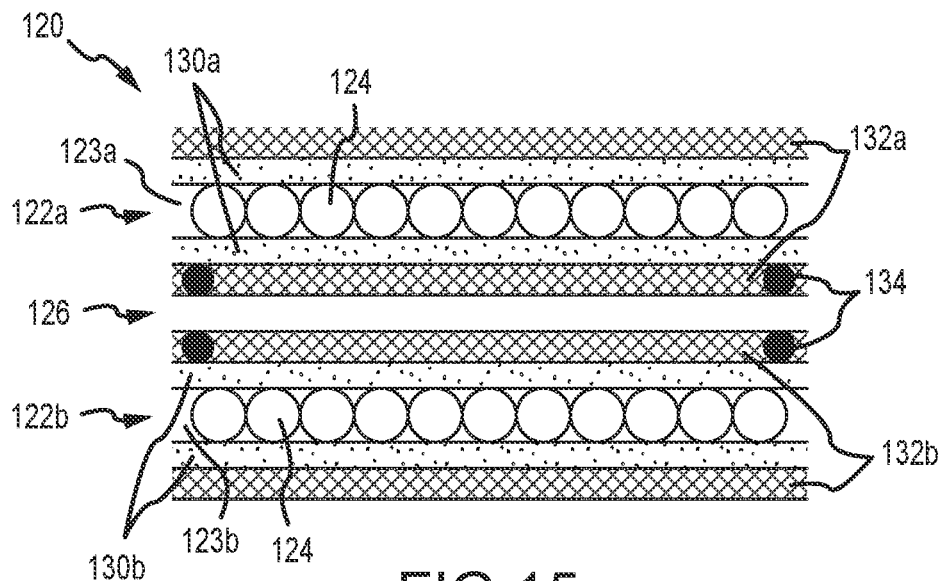
FIG.15
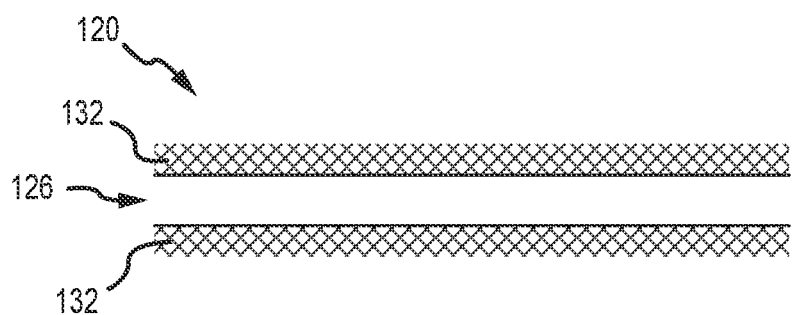
FIG.16
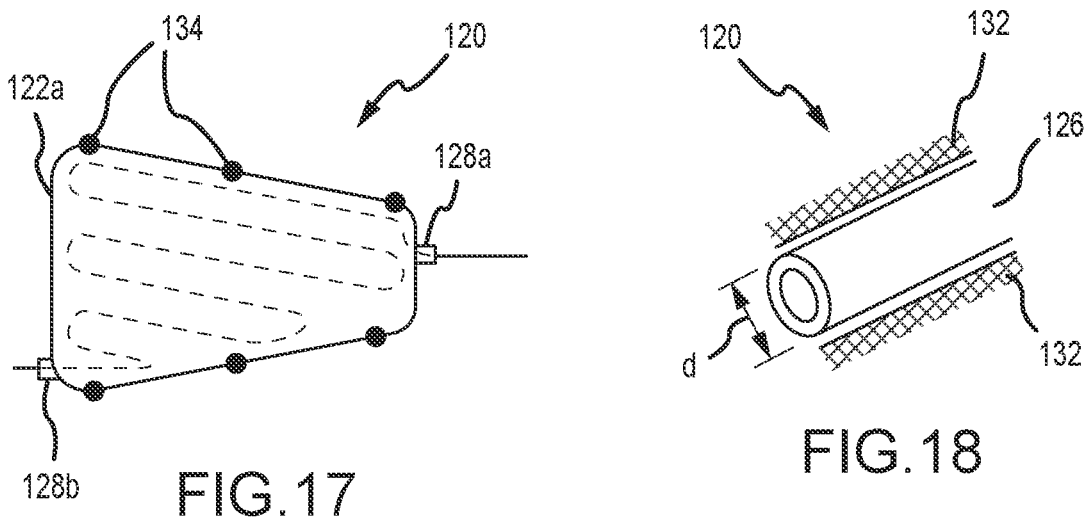
FIG.17
FIG.18

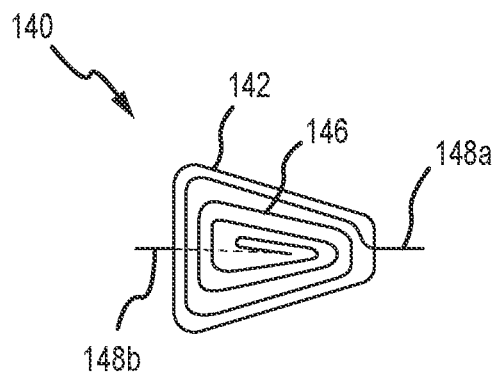 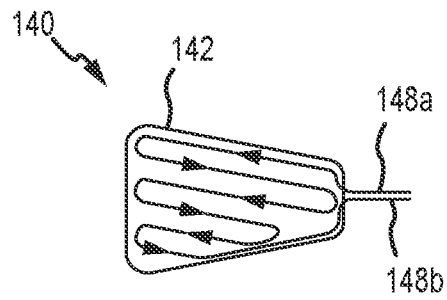
FIG.27  FIG.28
FIG.29
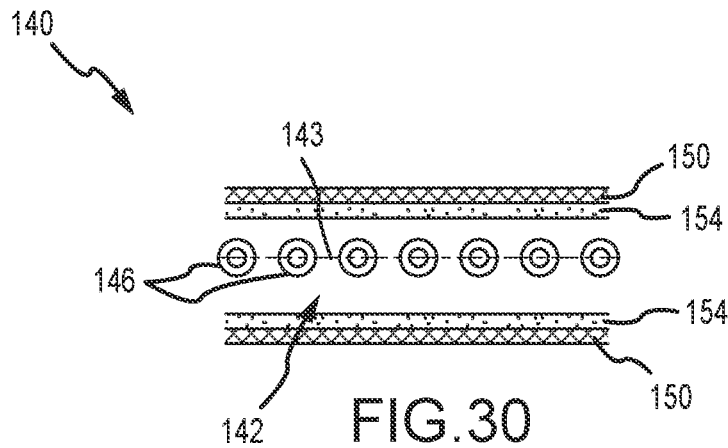
FIG.30

METHODS AND SYSTEMS FOR ENCAPSULATION DEVICES FOR HOUSING CELLS AND AGENTS

CROSS-REFERENCE TO RELATED APPLICATIONS

This U.S. Non-Provisional Application claims the benefit of priority from U.S. Provisional Patent Application Ser. No. 63/108,017 filed Oct. 30, 2020, the entire disclosure of which is hereby incorporated by reference.

FIELD

Embodiments of the present disclosure relate to implantable medical devices. In some embodiments, implantable encapsulation devices are provided that are operable to house cells, tissue, and/or therapeutic agents and deliver therapeutic effects to a host or recipient of the device.

BACKGROUND

The number of patients suffering from Type I and Type II diabetes is estimated to affect about 4.6% of the world's population. Pancreas transplantation and islet transplantation are known methods for treating diabetes. However, pancreas and islet transplantation into diabetic patients is limited to a small percent of patients who might benefit from either procedure due to the lack of available human pancreata or pancreatic islets. With the recent development of insulin secreting cells derived from human stem cells, there is a possibility of treating patients with insulin dependent diabetes through transplantation. However, such cells would be subject to rejection by the immune system of the recipient patient unless immunosuppressive drugs were administered to the patient for the rest of their life. Alternatively, insulin secreting cells could be provided with an immuno-isolating implantable device and placed in the diabetic patient to act as an insulin delivery source.

Since the islet transplantation protocol was established, clinical islet transplantation has been regarded as a treatment method for treating type 1 diabetics. However, the low engraftment success of transplanted islet cells remains a major cause of failure of long-term blood sugar regulation. Upon implantation, it is necessary for islet cells to be successfully engrafted through revascularization and blood flow regulation within a few days after transplantation. However, transplanted islet cells are exposed to a state with low vascular density and insufficient oxygen conditions, making it difficult to achieve normal engraftment of islet cells and the ability to achieve regulated insulin secretion in the patient.

Currently, there are limited means and materials to effectively implement live cell containing immuno-isolation devices in vivo. Limitations associated with supply of adequate oxygen levels to encapsulated cells, sufficient nutrient levels to the encapsulated cells, insufficient vascularization of the implanted device and immune response to the implant, remain barriers to use of cell-containing implantable devices.

SUMMARY

Embodiments of the present disclosure provide encapsulation devices having a matrix or scaffold for supporting cells. In some embodiments, methods of preparing and forming an encapsulation device with a matrix are provided.

Donor islet cells (e.g. from a cadaver) have been observed to "clump" together and function normally when implanted into an encapsulation device, while cells derived from differentiation of stem cells (for example) do not function as well as cadaver cells. Accordingly, embodiments of the present disclosure contemplate and provide one or more matrix structures within a void or cell-receiving area of the device. Matrices of the present disclosure provide a structural means of stabilizing and aggregating cells.

International Application Nos. PCT/US2017/060036 to Papas, PCT/US2017/060034 to Papas, PCT/US2017/060041 to Papas, and PCT/US2017/060043 to Papas relate to encapsulation devices and are each incorporated by reference in their entireties herein for all purposes.

Devices of the present disclosure include various materials, including those deemed appropriate by a person skilled in the art for an implantable medical device. For example, membranes of the present disclosure are contemplated as being prepared from a polymeric material. In such embodiments, the single layer gradient membrane is prepared from such polymeric materials as: polysulfone, polyarylethersulfone (PAES), polyethersulfone (PES), cellulose ester (cellulose acetate, cellulose triacetate, cellulose nitrate), nanocellulose, regenerated cellulose (RC), silicone, polyamide (nylon), polyimide, polyamide imide, polyamide urea, polycarbonate, ceramic, titanium oxide, aluminum oxide, silicon, zeolite (alumosilicate), polyarylonitrile (PAN), polyethylene (PE), low density polyethylene (LDPE), polypropylene (PP), polytetrafluoroethylene (PTFE), polyvinylidene fluoride (PVDF), polyvinylchloride (PVC), polypiperazine amide, polyethylene terephthalate (PET), polycarbonate (PC), polyurethane, and any complex or mixtures thereof. In particular embodiments, a single layer gradient membrane includes a polymeric material including polytetrafluoroethylene (PTFE). In certain preferred embodiments, PTFE is provided for at least a vascularizing layer of devices of the present disclosure. Additional materials are contemplated as being provided in membranes and implants of the present disclosure in addition to or in lieu of PTFE.

The advantages of the presently disclosed immune-isolation implantable devices include a maximization of surface area presented by the device available for vascularization by a host. In particular, implantable devices or portions thereof that include an immuno-isolation device present a surface area that may be vascularized by the host when implanted. This structure maximizes vascularization of the device as a whole in the animal.

In one embodiment, a method for filling an implantable encapsulation device including an internal void for encapsulation of cells, a channel adjacent a first side of the void and separated from the void by a fluid permeable membrane, and a vascularization membrane on a second side of the void is provided. The method includes introducing a composition including cells and a matrix-forming material into the void; introducing a cross-linking agent into the channel, whereby the cross-linking agent passes the fluid permeable membrane to cross-link the matrix-forming material near the fluid permeable membrane; introducing a quenching agent into the channel, whereby the quenching agent passes the fluid permeable membrane to reduce cross-linking of the matrix-forming material, whereby the void includes a matrix gradient having higher cross-linking near the fluid permeable membrane and lower cross-linking density near the vascularization membrane.

In one embodiment, an implantable encapsulation device is provided that includes a first void for receiving and encapsulating cells, wherein the first void has a first side; a channel adjacent the first side of the first void and separated from the first void by a gas permeable membrane; wherein the channel occupies a portion of the first side of the first void that is less than all of the first side of the first void; and wherein the portion of the first side of the first void not occupied by the channel includes a vascularization membrane.

In various embodiments, methods of preparing, preserving, freezing and/or thawing encapsulation devices are provided. In some embodiments, methods are provided that include introducing a cryopreservation solution to freeze cells within a matrix or encapsulation device. It is contemplated that cryopreservation solution is provided to an encapsulation device to affect a transfer of thermal energy and reduce the temperature of the device and associated cells. In preferred embodiments, a cryopreservation solution is delivered through one or more channels that extend in or through a volume of an encapsulation device. It is contemplated that cryopreservation solution(s) are applied to the device in a flow-through manner in which solution is continuously applied through the device and/or solution is delivered through an opening and allowed to remain static while cooling occurs. Additionally, methods and systems of the present disclosure further contemplate the provision of applying cryopreservation solution(s) to an exterior of an encapsulation device in lieu of or in addition to the application of solution(s) to the gas chamber.

In some embodiments, the cryopreservation solution includes dimethyl sulfoxide. The solution(s) are contemplated as including various different concentrations of dimethyl sulfoxide and, in various embodiments, include dimethyl sulfoxide provided with or diluted in additional fluid.

Embodiments of the present disclosure further contemplate delivering a fluid (gas or liquid) to increase thermal energy within the device and/or cells. For example, it is contemplated that gas (e.g. ambient air) or liquid is provided in or through a gas chamber of an encapsulation device to thaw or otherwise increase a temperature of the device and housed cells. Accordingly, the present disclosure is not limited to methods of freezing or cooling devices and cells.

In various embodiments of the present disclosure, encapsulation devices are provided with a cell matrix for housing, supporting, and promoting proper functioning of cells. In various embodiments, a matrix-forming material, such as alginate, is provided through a flow channel or internal conduit to form a matrix with a greater density proximal to the gas chamber and a decreasing density (at least in terms of cross-linking) at distances farther away from the channel and membrane between the channel and the matrix. Methods of forming a matrix and preparing an encapsulation device are provided that initiate matrix creation at or near an interior of the device and proximal to the channel, and wherein the matrix density is less at points distal from the channel. Such embodiments allow for solution(s) to be provided to the device through the flow channel or chamber while reducing risk that the solution(s) will block or clog the membranes and prevent gas delivery (for example) into the matrix. Various embodiments of the present disclosure contemplate the provision of a flow channel and the use of that channel for multiple purposes. For example, systems and methods of the present disclosure contemplate applying and conveying a cryopreservation solution to or through the channel to freeze the device and housed cells. The channel(s) of such devices must later be available for receiving fluid (e.g. oxygen-carrying gas) to deliver necessary materials to the cells as shown and described herein in various embodiments. Accordingly, processes related to cryopreservation and the application of cryopreservation solution(s) preferably avoid clogging or obstructing the channel, the membrane, and the matrix. In various embodiments, methods of the present disclosure include treating or washing encapsulation subsequent to cryopreservation or thawing steps. In some embodiments, sodium chloride is applied to the exterior surfaces and/or inner channel of a device to wash or treat the device and remove any dimethyl sulfoxide (or other materials) that may be present on the device and which may have undesirable impacts on the cells if not removed or remedied.

In some embodiments, matrix formation is provided wherein calcium chloride is provided within a flow channel of an encapsulation device and sodium chloride is provided or injected into the cell chamber of the device to form a matrix with a desired gradient or density distribution. A gradient is formed by the interaction between calcium chloride and sodium chloride, and wherein the matrix includes a greater density proximal to the channel.

In one embodiment, a method is provided for filling an implantable encapsulation device including an internal void for encapsulation of cells, a channel adjacent a first side of the void and separated from the void by fluid permeable membrane, and a vascularization membrane on a second side of the void. The method includes introducing a composition including cells and a matrix-forming material into the void and introducing a cross-linking agent into the channel, whereby the cross-linking agent passes the fluid permeable membrane to cross-link the matrix-forming material near the fluid permeable membrane. A quenching agent is introduced at least one of into the channel or to surround the chamber, whereby the quenching agent passes the fluid permeable membrane to reduce cross-linking of the matrix-forming material, whereby the void includes a matrix gradient having higher cross-linking near the fluid permeable membrane and lower cross-linking density near the vascularization membrane.

In one embodiment, an implantable encapsulation device is provided that includes a first void for receiving and encapsulating cells. The first void has a first side and a channel adjacent the first side of the first void and separated from the first void by a gas permeable membrane. The channel occupies a portion of the first side of the first void that is less than all of the first side of the first void. The portion of the first side of the first void not occupied by the channel includes a vascularization membrane.

In one embodiment, a method is provided for preparing an implantable encapsulation device is provided wherein the device includes first and second chambers for encapsulation of cells; a channel adjacent first exterior surfaces of the first and second chambers and separated from interiors of the chambers by at least one fluid permeable membrane; and wherein the first and second chambers have second exterior surfaces. The method includes introducing a composition including cells into the interiors of the chambers, delivering a fluid into the channel to increase or decrease a temperature of the cells, and delivering a fluid across the second exterior surfaces of the first and second chambers to increase or decrease a temperature of the cells.

Various concepts disclosed herein may be provided in combination with one another even if such combination is not specifically depicted or described. For example, and without limitation, cryopreservation and fluid delivery concepts may be provided with the device of FIG. 5 even if not specially shown and described.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In addition, the materials, methods, and examples are illustrative only and are not intended to be necessarily limiting.

DESCRIPTION OF THE DRAWINGS

FIG. 15 is a cross-sectional elevation view of an implantable encapsulation device and related methods according to embodiments of the present disclosure.

FIG. 16 is a cross-sectional elevation view of an implantable encapsulation device and related methods according to embodiments of the present disclosure.

FIG. 17 is a cross-sectional top plan view of an implantable encapsulation device and related methods according to embodiments of the present disclosure.

FIG. 18 is a perspective view of portions of an implantable encapsulation device and related methods according to embodiments of the present disclosure.

FIG. 27 is a cross-section top plan view of an implantable encapsulation device and related methods according to embodiments of the present disclosure.

FIG. 28 is a cross-section top plan view of an implantable encapsulation device and related methods according to embodiments of the present disclosure.

FIG. 29 is a cross-sectional elevation view of an implantable encapsulation device and related methods according to embodiments of the present disclosure.

FIG. 30 is a cross-sectional elevation view of an implantable encapsulation device and related methods according to embodiments of the present disclosure.

DETAILED DESCRIPTION

Reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

Figure 1:
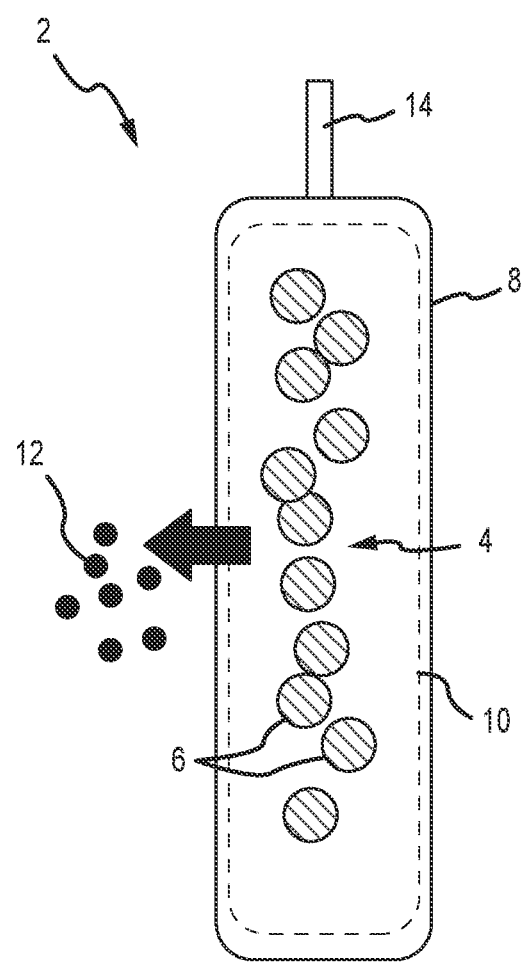
FIG. 1 is a cross-section of an encapsulation device with at least one port according to embodiments of the present disclosure.

FIG. 1 is a cross-sectional elevation view of an encapsulation device 2 according to embodiments of the present disclosure. As shown, the device 2 includes an internal volume or void 4 that is operable to receive and house cells 6 or tissue. The device 2 further includes at least one membrane 8. In some embodiments, the at least one membrane 8 includes a vascularization membrane that is impermeable to cells. In certain embodiments, an immunoisolation membrane 10 is also provided. Non-cell factors or molecules 12 may escape or pass through the membrane(s) 8, 10, while cells 6 are contained. At least one port 14 is provided, and the port allows for access to the internal volume 4 of the device. The port 14 may be utilized to load cells and tissue into the device, for example. The entire device 2 is operable to be implanted into a patient (e.g. a human patient). The device 2 is preferably sized and operable to be subcutaneously inserted into a patient, where a device function including, but not limited to, the egress or leaching of non-cell factors 12 provides therapeutic effects to the patient. Various embodiments of the present disclosure provide encapsulation devices having a vascularization membrane and an immunoisolation membrane. Certain embodiments provide encapsulation devices having only a vascularization membrane to allow blood vessels to grow into tissue.

Figure 2:
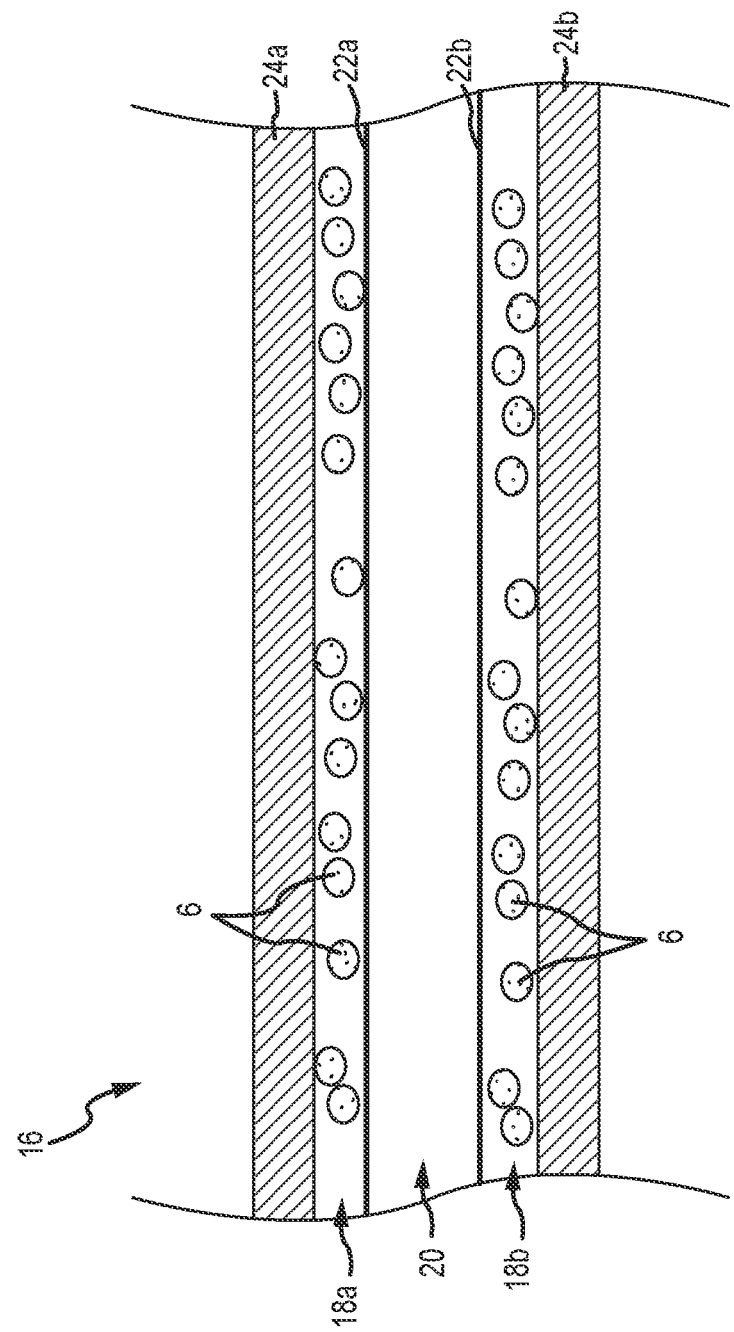
FIG. 2 is a cross-sectional view of an encapsulation device according to embodiments of the present disclosure.

FIG. 2 is a cross-sectional elevation view of an encapsulation device 16 according to embodiments of the present disclosure. In this embodiment, two internal voids or chambers 18a, 18b housing cells 6 are shown. The voids may be accessed for the introduction of cells through ports (not shown). Between the voids 18a, 18b is a fluid channel 20 for introduction of a fluid, either gas or liquid, as described further below. In one embodiment, upon transplantation, oxygen may be introduced into channel 20 for maintaining the cells in a viable and functional state. For example, oxygen may improve the viability of the cells, while also promoting functionality of the cells including, but not limited to, insulin secretion. Other uses and configurations of channel 20 are provided herein. Channel 20 may be accessed for the introduction of fluids through ports (not shown). Between channel 20 and voids 18a, 18b is a membrane 22a, 22b through which fluids in channel 20 may pass into voids 18a, 18b. For example, the membrane 22a, 22b may be a fluid-permeable membrane. In some embodiments, the membranes 22a, 22b are constructed from materials such as polytetraflouroethylene (PTFE) or other similar material (e.g., as described throughout the present disclosure). The encapsulation device 16 further may further include layers 24a, 24b, each of which may include an immunoisolation membrane and a vascularization membrane, the functions of which are described elsewhere herein. Devices of the present disclosure, including those shown in FIG. 2, are contemplated as including a mesh or other structural support element(s) surrounding all or part of the encapsulation device 16.

In various embodiments, including those shown in FIGS. 1-2, cells are provided within an encapsulation device and the cells include a diameter of between approximately 5-15 micrometers (μm). In some embodiments, devices include spheroids or aggregates of cells including dimensions of between approximately 50 and 500 microns. In some embodiments, vascularization membranes are provided with pore sizes of about 5-10 μm, and the immunoisolation membrane includes pore sizes of about 0.2-0.6 μm. The immunoisolation membrane is contemplated as including a thickness of about 20-40 μm, and the vascularization membrane may have of thickness of about 10-100 μm, and preferably about 30 μm with pore sizes of between approximately 0.1 μm and 1.0 μm (and preferably of about 0.4 μm). In some embodiments, the membranes are constructed from materials such as polytetraflouroethylene (PTFE) or other similar material (e.g., as described throughout the present disclosure). The present disclosure and embodiments described herein are not limited to the aforementioned pore sizes and thicknesses of the membranes. For example, International Application PCT/US2017/060036 to Papas, which is previously hereby incorporated by reference in its entirety, discloses various structures and dimensions for implants and membranes which are contemplated for use herein.

Devices of the present disclosure are contemplated as including various shapes and sizes and as having internal voids with various different internal volumes. For example, in some embodiments, the void has a volume of between about 4.5 μL and about 400 μL, or any intermediate range between those endpoints. In some embodiments, encapsulation devices of the present disclosure include a length of between about 2 and about 10 cm, or any intermediate range, such as between about 4 and about 5 cm. In addition, encapsulation devices of the present disclosure include a width of between about 1 and about 5 cm, or any intermediate range, such as between about 2 and about 3 cm. Thus, the encapsulation devices may be generally rectangular (or other geometric shape, e.g., polygonal) with a thickness sufficient to accommodate the layers of membranes and voids.

In various embodiments, cells 6 provided within an encapsulation device are contemplated as including islet cells or stem cell derived beta cells or the like, e.g., for regulating blood glucose, or other cells or spheroids that may produce and release a therapeutic agent that is useful in the body. The cells in the different encapsulation devices may be the same, similar, or various different combinations of cells may be included within the encapsulation devices or throughout the device(s). For example, in embodiments including a plurality of encapsulation devices, the cells in the first encapsulation device may be the same as the cells in the second encapsulation device. Or, in some embodiments, the cells in the first encapsulation device may be the different from the cells in the second encapsulation device.

Figure 3:
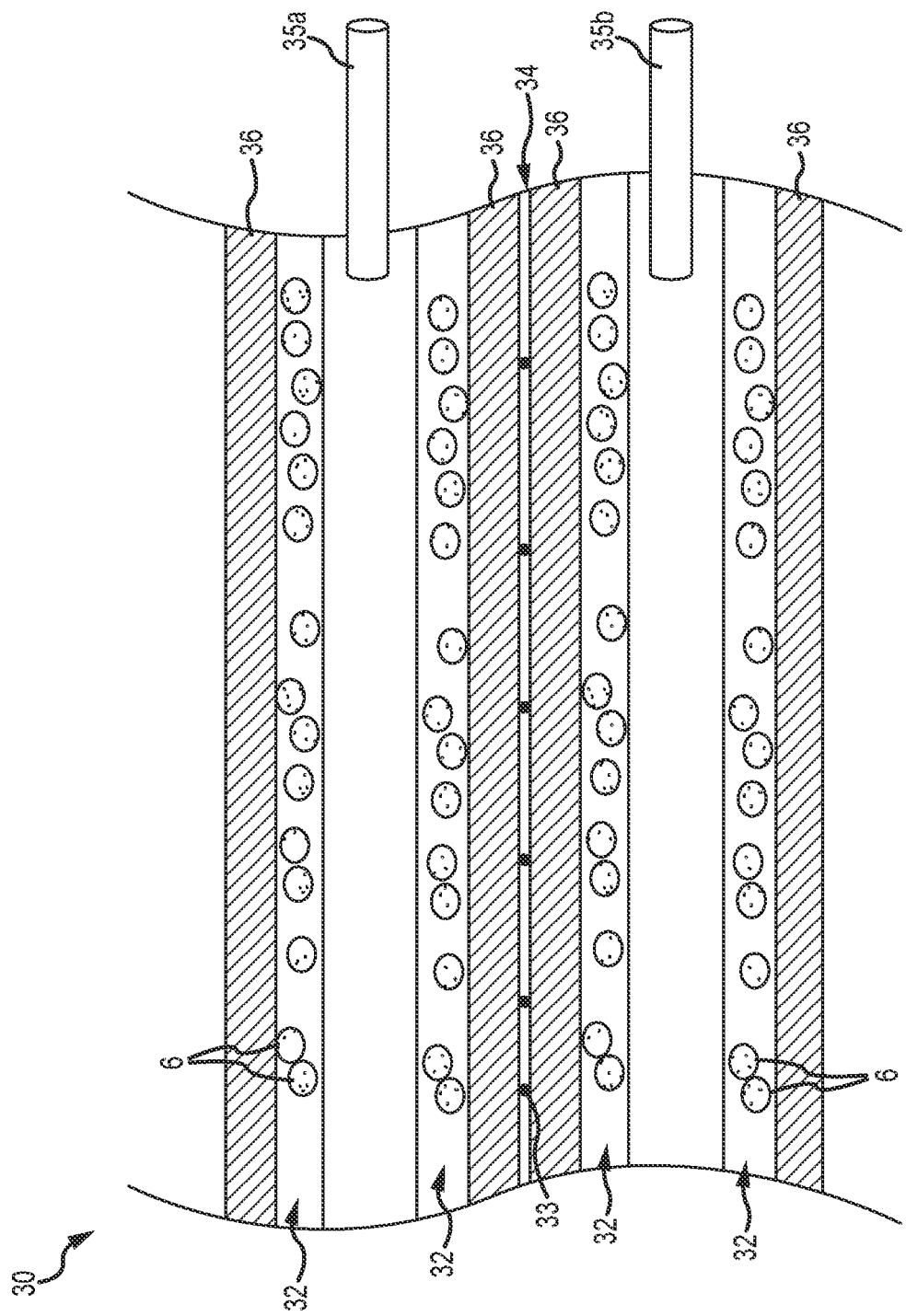
FIG. 3 is an elevation view of an encapsulation device according to embodiments of the present disclosure.

FIG. 3 is a cross-sectional elevation view of an encapsulation device 30 according to embodiments of the present disclosure. As shown, the device 30 includes a plurality of layers and spaced apart voids 32. The layers and voids 32 may be secured by sutures, a kinetic glue, or welded together (e.g., spot welded, or the like) with space 34 provided to permit vascularization. In some embodiments, including that shown in FIG. 3, a plurality of spot welds 33 are provided to join or attach features of the device. For example, two or more of the devices shown in FIG. 2 may be provided and secured together by spot welds 33 or various other securing means. The spot welds 33 provide for a connection while still allowing for and providing void spaces 34 between and around points of attachment within which vasculature may grow and extend. Vasculature 36 is allowed to form and provides a means of oxygen transmission to cells within the device at least after implantation. A plurality of ports 35a, 35b are provided for loading cells (e.g., through ports) and/or providing a flow of fluid (e.g. oxygen gas) such as through port to internal components of the device 30.

Figure 4:
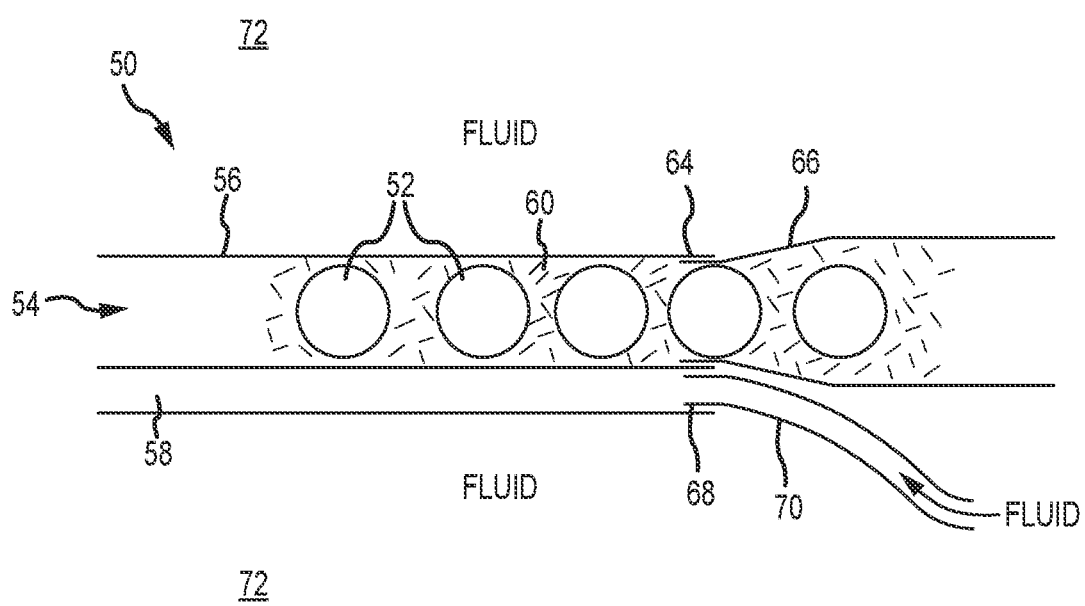
FIG. 4 is a cross-sectional elevation view of a portion of an encapsulation device according to embodiments of the present disclosure.
Figure 5:
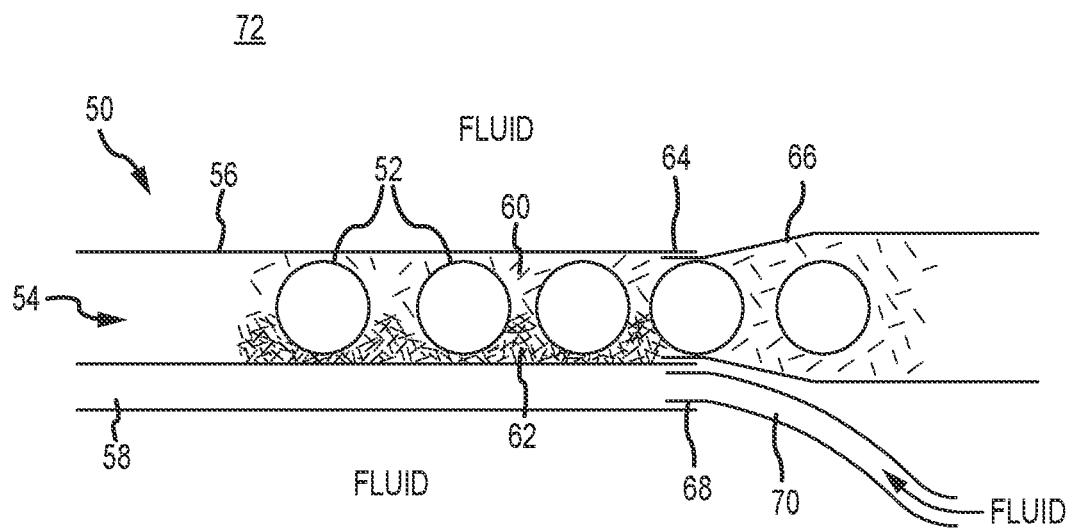
FIG. 5 is a cross-sectional elevation view of a portion of an encapsulation device according to embodiments of the present disclosure.
Figure 6:
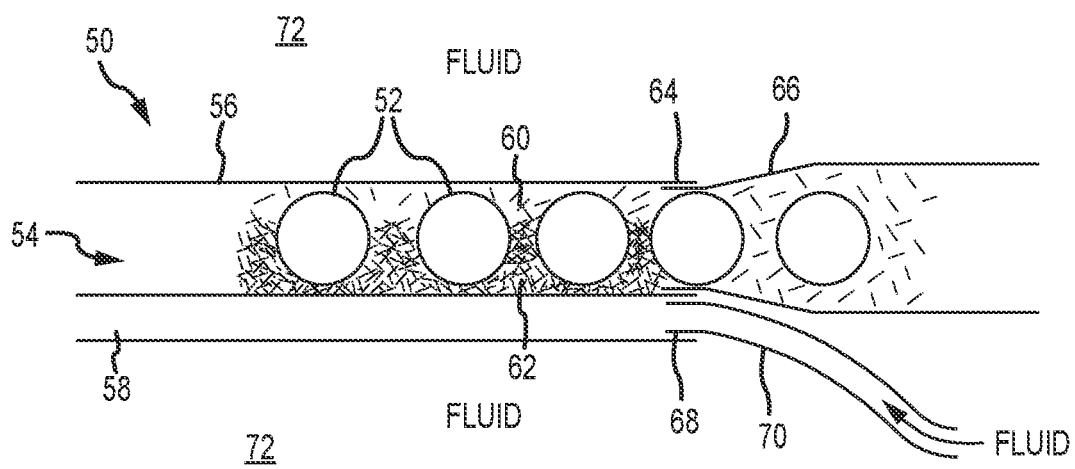
FIG. 6 is a cross-sectional elevation view of a portion of an encapsulation device according to embodiments of the present disclosure.

FIGS. 4-6 illustrate embodiments according to the present disclosure relating to the formation of a matrix within a void for embedding or aggregating cells in a graduated matrix by use of a fluid channel and a void for housing of cells. In particular, FIG. 4 is a cross-sectional elevation view of an encapsulation device 50 and method of using the same. As shown, an encapsulation device 50 is provided with cells 52. The cells 52 are provided and housed in an internal void 54 of the device. The cells may be provided in the form of spheroids including multiple cells within each spheroid. Alternatively, individual cells or "clumps" of cells may be loaded into the voids 54 of the device.

In addition to loading cells 52 into the void 54, the embodiments further include introducing a solution including a matrix-forming material so that the void, including the area immediately surrounding the cells, is provided with a matrix-forming material that may form a hydrogel or other similar matrix. For example, the matrix-forming material may be a monomeric or polymeric material that upon introduction of a binder or crosslinker forms a hydrogel or other matrix. In some embodiments, the matrix-forming material may be alginic acid or other polysaccharide or fibrinogen that may form alginate or fibrin gels. U.S. Pat. No. 9,642,814 to Ramachandran et al., which is hereby incorporated by reference in its entirety, discloses various processes and materials for matrix formation.

The void is bounded by at least one membrane 56. The membrane 56 preferably surrounds and encapsulates the void 54 but is shown as an upper and lower-layer in the cross-section of FIG. 4. A channel 58 is provided adjacent to the membrane, and the channel 58 is operable to receive and convey fluids including gases. In this state, the matrix-forming material has not yet formed a membrane, and in various embodiments, systems and methods are provided wherein oxygen gas is conveyed to and through the channel 58. The oxygen is provided to maintain viability of the cells and is allowed to diffuse across the membrane 56. In some embodiments, the channel is provided as a confined tubular channel. In preferred embodiments, the channel 58 is provided as a gap or space between adjacent membranes, only one of which is shown in FIG. 4 in which a second void 54 is adjacent channel 58 and opposite the first void 54.

The channel 58 is provided adjacent to the void 54 and is separated by the membrane 56. Oxygen is provided and allowed to flow through the channel. Oxygen is allowed to diffuse through the membrane and infiltrate at least a portion of the void 54.

In various embodiments according to the present disclosure, and as shown in FIG. 5, methods and systems—contemplate interrupting or stopping the flow of oxygen. A cross-linking agent (e.g. calcium chloride, or $CaCl_2$)) that is specific to cause the matrix-forming material 60 provided in the void 54 to form a matrix, is then injected into the channel 58. As the cross-linking agent diffuses through the membrane 56, it reacts with and activates the matrix-forming material 60 to become cross-linked and form a matrix 62 to support the cells and promote proper function. As shown in FIG. 5, an area or portion of the matrix-forming material around a portion of the cells 52 and closest to the membrane is caused to be cross-linked first and to a greater degree than a portion of the matrix-forming material that is spaced apart from the channel 58.

The present disclosure contemplates various materials for forming a matrix or scaffold. For example, in some embodiments glutaraldehyde (GA) is used as a crosslinking agent for improving biocompatibility and durability. In various embodiments, other crosslinking agents are contemplated. An ideal biomaterial crosslinking agent includes no cytotoxicity and includes a low-cost material. Preferably, the agent improves the mechanical performance of the materials. Various chemical crosslinking agents and natural cross-linking agents are contemplated. For example, contemplated chemical crosslinking agents include, but are not limited to, glutaraldehyde (GA), carbodiimide (1-ethyl-3-(3-dimethyl aminopropyl)-carbodiimide (EDC)), epoxy compounds, six methylene diisocyanate, glycerin and alginate, or the like. In addition, contemplated natural crosslinking agents include, but are not limited to, genipin (GP), nordihydroguaiaretic acid (NDGA), tannic acid and procyanidins (PC). Various concentrations of crosslinking agents are contemplated herewith and no limitation with respect to an amount, proportion, or concentration of any particular crosslinking agent is provided. Additionally, no limitation with respect to agents is provided herewith. It is contemplated that various agents and materials are provided to form a matrix or scaffold as shown and described herein. For example, various plasma gels are contemplated for use. Commercially available products such as SURGIFLO® Hemostatic Matrix and Grifols VISTASEAL® are contemplated as clotting or cross-linking agents for use with systems and methods of the present disclosure. Matrices and devices of the present disclosure are contemplated as being biodegradable in various embodiments. In other embodiments, the matrices and devices are contemplated as being substantially non-biodegradable, permanent features.

When sufficient cross-linking and matrix formation has occurred such that the cells are embedded or bound in the matrix and the distal portions of the cells 52 are not provided in the matrix, or the matrix is of an appropriate density to allow passage of and proper kinetics of glucose and insulin, provision of the cross-linking agent is stopped. In addition, matrices formed by practice of the invention may have a thickness of between about 10 μm and about 600 μm, or any intermediate range thereof. As shown in FIG. 6, the channel 58 is then provided with a fluid or quenching agent to quench the matrix-forming reaction between the cross-linking agent and the matrix-forming material. In some embodiments, the quenching agent is contemplated as including physiological saline and the matrix includes an alginate matrix. The introduction of the quenching agent serves to limit or intentionally stop the growth and formation of the matrix 62 once the matrix has reached a desired state. It is noted herein a fluid or quenching agent (e.g., saline, or the like) may be introduced to surround an exterior of the membrane 56 in addition to or instead of into the channel 58 to inhibit crosslinking and matrix formation within the membrane 56, while also further enhancing the gradient strength of the formed matrix 62. For example, the device may be bathed in a media or a physiological saline that does not crosslink including, but not limited to, sodium alginate.

In one example embodiment, the cells 52 may be loaded via an opening 64 of the void 54 via a loader 66. In addition, the fluid or quenching agent may be introduced into the channel 58 via an opening 68 in the channel 58 by tubing 70 (e.g., removable tubing). Further, the fluid or quenching agent may surround the chamber 56 and/or the channel 58 within a bath or containment device 74.

Methods, systems and devices as shown in FIGS. 4-6 (for example) improve the function of stem cell-derived islet cells by artificially forming a matrix without physically impairing their basic function of releasing insulin when glucose is bound. In some embodiments, the matrix includes a hydrogel matrix, and the cross-linking agent includes a divalent ion such as calcium. In further embodiments, the matrix includes a fibrin matrix, the cross-linking agent includes thrombin, and a quenching agent includes a thrombolytic agent. In some embodiments, the matrix includes an alginate and at least one of calcium chloride, barium chloride, and strontium chloride is used as the cross-linking agent, and saline or sodium chloride is used as the quenching agent. In various embodiments of the present disclosure, methods of preparing encapsulation devices with cells embedded in a graduated density matrix are provided. In some embodiments, the matrix is less dense near a surface of cell-containing chamber that is vascularized and/or exposed to the body. In certain embodiments, methods include providing a channel with specific agents in the specific order or sequence shown and described with respect to FIGS. 4-6. In certain embodiments, it is contemplated that agents are provided to the gas channel for predetermined amounts of time based on the specific materials provided and the amount of matrix formation that is desired. Specifically, since it is contemplated that various method steps of the present disclosure will be performed without the physical ability to view or actively monitor the extent of matrix formation, materials are delivered through the channel 58 for specific time periods.

Additional embodiments according to the present disclosure includes an implantable encapsulation device including an internal chamber for encapsulation of cells, a channel adjacent a first side of the chamber and separated from the chamber by fluid permeable membrane, and a vascularization membrane on a second side of the chamber, wherein the chamber includes a matrix gradient having higher crosslinking near the fluid permeable membrane and lower crosslinking density near the vascularization membrane. Still further additional embodiments according to the disclosure is the implantation of such an encapsulation device into a patient in need thereof to provide a therapeutic benefit to the patient.

FIGS. 7-12 illustrate embodiments according to the present disclosure relating to an encapsulation device in which a channel for delivery of a fluid (such as oxygen, a cross-linking agent, a quenching agent, a cryopreservation solution, etc.) is configured to allow for vascularization between cell-containing chambers in a device, while still maintaining a channel for the delivery of fluids. By allowing for the vascularization between two cell-containing chambers in an encapsulation device, a greater amount of the surface area of the cell-containing chamber is exposed to vascularization and therefore, the biological functioning of the device may be increased.

Figure 7:
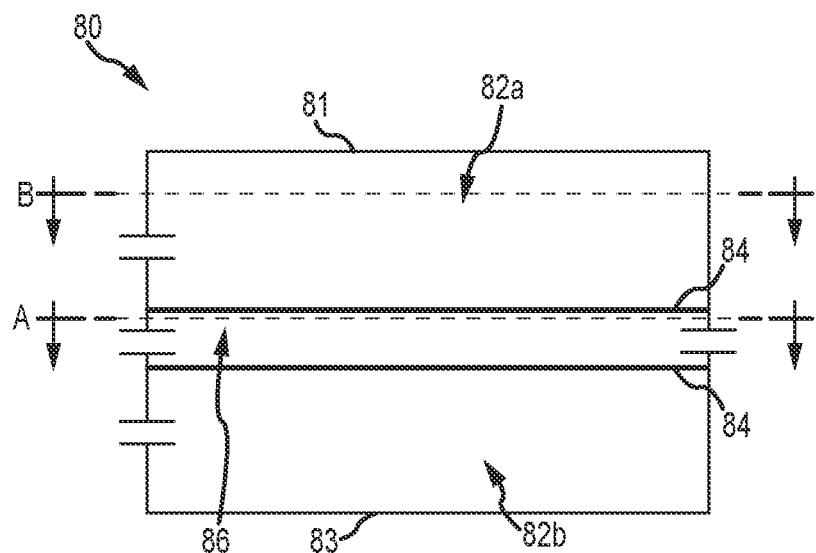
FIG. 7 is an elevation view of an implantable encapsulation device according to embodiments of the present disclosure.

FIG. 7 is a side elevation view of an encapsulation device 80 having upper 81 and lower 83 surfaces. As shown in FIG. 7, the encapsulation device 80 includes a multi-layered device having a plurality of internal chambers 82a, 82b separated by membranes 84. A channel 86 is provided for delivering fluids (e.g. oxygen gas) to the encapsulation device 80. The device 80 includes ports 88 for introduction of cells into chambers 82a, 82b. In some embodiments of encapsulation devices of the present disclosure, the "footprint" of the channel 86 is the same or approximately the same as the footprint of the chambers 82a, 82b, however, the disclosure also contemplates a channel 86 that has a smaller footprint, for example, more narrow, so that the chambers 82a, 82b extend beyond the channel 86 in a manner that there is open space between the chambers 82a, 82b outside of the channel 86. Such open space exposes surfaces of the chambers 82a, 82b to allow for vascularization thereon. In such embodiments, to reduce the footprint of the channel 86, the one channel be a non-linear arrangement or path. In such embodiments, curvilinear channels may include peaks and troughs. In use, after implantation of the device 80 and vascularization of upper and lower surfaces 81, 83, as well as vascularization between the chambers 82a, 82b, oxygen may no longer need to be delivered through the channel 86.

Figure 8:
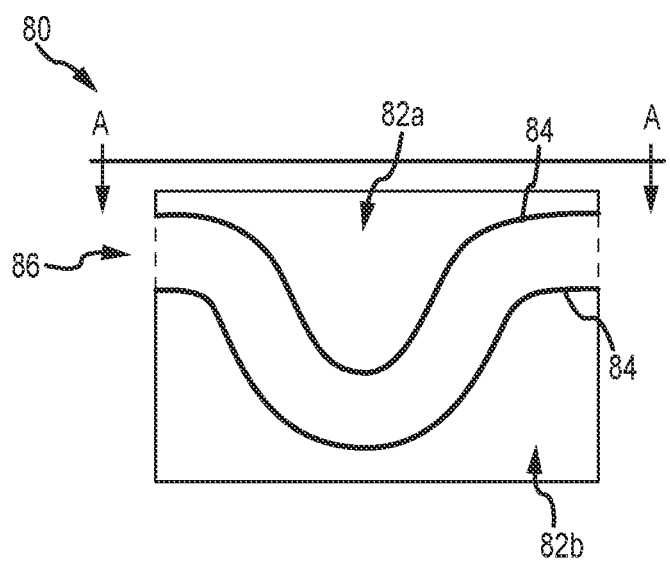
FIG. 8 is a cross-sectional elevation view of an implantable encapsulation device according to embodiments of the present disclosure.

FIG. 8 is a cross-sectional elevation view of a portion of the encapsulation 80 device taken at line A-A of FIG. 7. As shown, a channel 86 extends through the device and void spaces or chambers 82a, 82b are provided. The footprint of the channel 86 is smaller than the footprint of the lower chamber 82b. For example, the footprint or area of the channel may be from about 10% to about 90%, or any intermediate range thereof, of the footprint of the lower or upper chamber. The void spaces 82a, 82b or exposed surface of the lower chamber 82b that does not have the serpentine channel 86 may have a vascularization membrane 84 provided to promote vascularization of that surface. Once vascularization has occurred in the device 80, it may no longer be necessary to provide oxygen to the channel 86. The supply of oxygen may therefore be terminated at a certain point, resulting in the cells no longer being supplied with oxygen other than from blood through the vascularization membrane. It is recognized that cells provided within the device 80 will benefit from having a greater oxygen supply than may be achieved through the outer sides of the voids 82a, 82b. Accordingly, in various embodiments, the channel 86 is provided in a curvilinear or serpentine shape and reduced in footprint so that some portion of the inner surfaces of the voids are exposed and may be vascularized. The portion of the inner surface of the void not occupied by the oxygen channel preferably includes both an immunoisolation layer and a vascularization layer.

Figure 9:
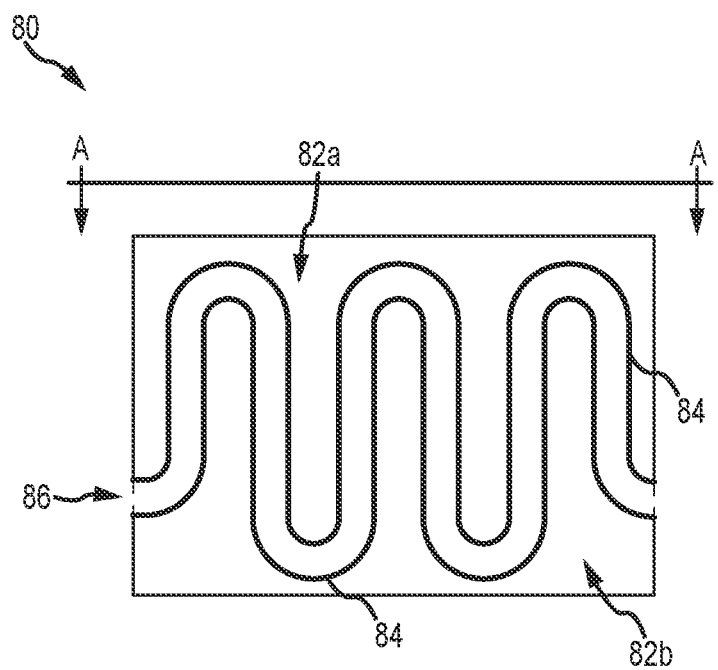
FIG. 9 is a cross-sectional elevation view of an implantable encapsulation device according to embodiments of the present disclosure.
Figure 10:
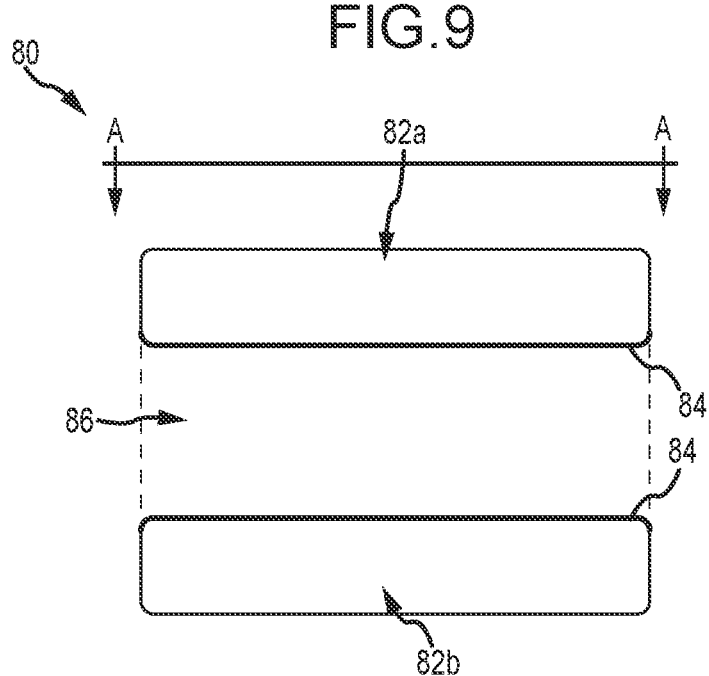
FIG. 10 is a cross-sectional elevation view of an implantable encapsulation device according to embodiments of the present disclosure.
Figure 11:
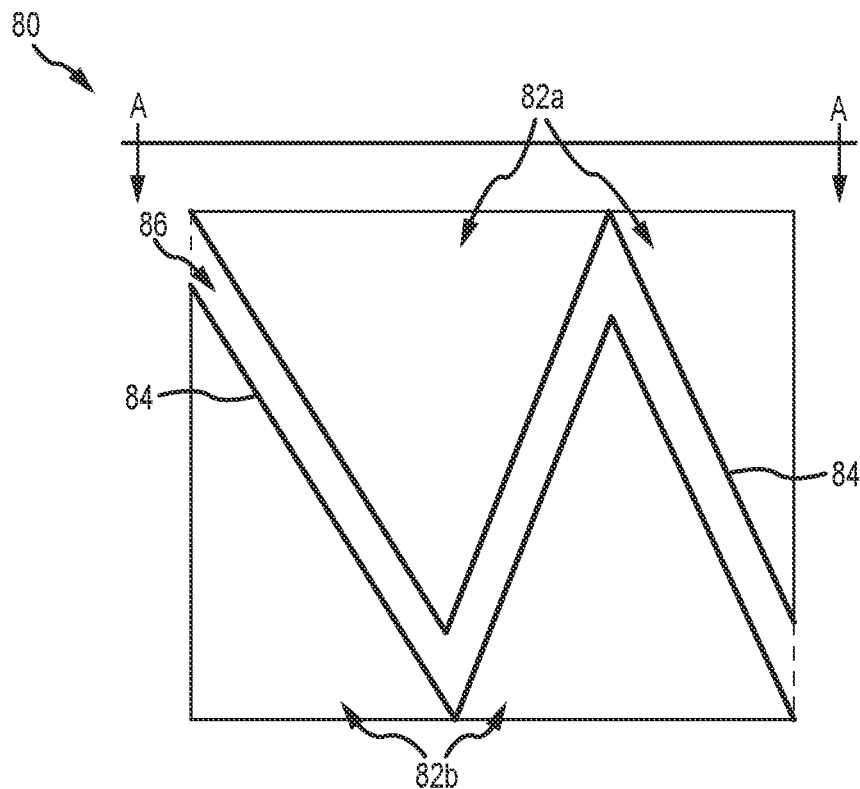
FIG. 11 is a cross-sectional elevation view of an implantable encapsulation device according to embodiments of the present disclosure.

FIG. 9-11 are cross-sectional views of encapsulation devices of alternative embodiments according to the present disclosure and taken at line A-A of FIG. 7. In particular, FIG. 9 shows a compact serpentine arrangement of a channel 86 with voids 82a, 82b on opposing sides of the channel 86 that may be vascularized. In addition, FIG. 10 shows a channel 86 bounded by first and second voids 82a, 82b. Further, FIG. 11 shows a zig-zag type channel 86 with voids 82a, 82b on opposing sides thereof.

Figure 12:
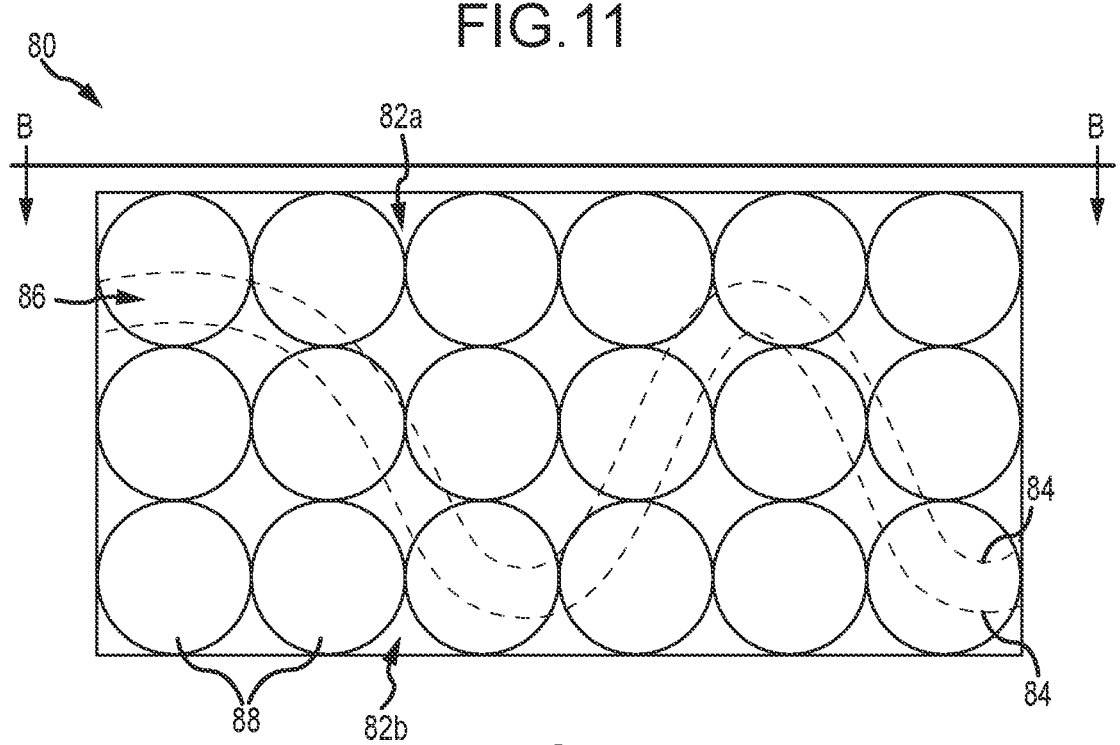
FIG. 12 is a cross-sectional elevation view of an implantable encapsulation device according to embodiments of the present disclosure.

FIG. 12 is a cross-sectional view of embodiments of an encapsulation device according to the present disclosure and taken at line B-B of FIG. 7. As shown, the channel 86 is shown in phantom and a plurality of cells 88 are provided. The cells may be provided in the form of spheroids including multiple cells within each spheroid. Alternatively, individual cells or "clumps" of cells may be loaded into the voids 82 of the device. As shown, a channel 86 is provided as an arcuate or serpentine channel to provide sufficient surface area of the channel for oxygen or other fluid delivery to cells 88. As shown in FIG. 12, a layer of cells includes a plurality of cells 88. In various embodiments, some of the plurality of cells 88 will not be in direct contact with the channel 86. However, appropriate oxygen delivery and distribution is provided to keep a sufficient number of cells alive during assembly, loading, and implantation of device. After vascularization of the upper and lower surfaces (81 and 83 in FIG. 7) of the device 80 has been achieved, oxygen delivery through channel 86 may be terminated and oxygen is provided to the cells via the vascularized membrane(s). The device and channels of FIGS. 8-12 provide for a reduced area oxygen delivery system as compared with certain devices of the prior art. Such devices may include oxygen delivery "layers" that are approximately the same in area as overall footprint of the device. In multi-layered encapsulation devices including those shown in FIGS. 2, 3 and 7-12, such an oxygen delivery member may function well while oxygen gas is flowing to the device. However, once the delivery of oxygen is terminated, these devices may limit the amount of vascularization and therefore limit later-stage delivery of oxygen to the cells (e.g., after implantation). To address this, embodiments of the present disclosure contemplate and provide oxygen delivery channels that extend through void spaces 82a, 82b, provide enhanced surface area for delivery of oxygen, and do not unduly limit vascularization of components of the device.

Although the embodiments of FIGS. 8-12 generally depict one gas channel 86 of an encapsulation device, the present disclosure is not limited to devices having a single gas channel. It is contemplated, for example, that a plurality of gas channels extend through and between void spaces 82 of the present disclosure. In embodiments including a plurality of gas channels, it is preferred that the gas channels are arranged or staggered in three-dimensions so as to not block, impede, or segregate a layer of cells from a vascularization membrane.

Another embodiment of the present invention includes implantation of an encapsulation device having a reduced fluid channel footprint as described herein into a patient in need thereof to provide a therapeutic benefit to the patient. In this embodiment, vascularization on the device between cell chamber layers is achieved.

Figure 13:
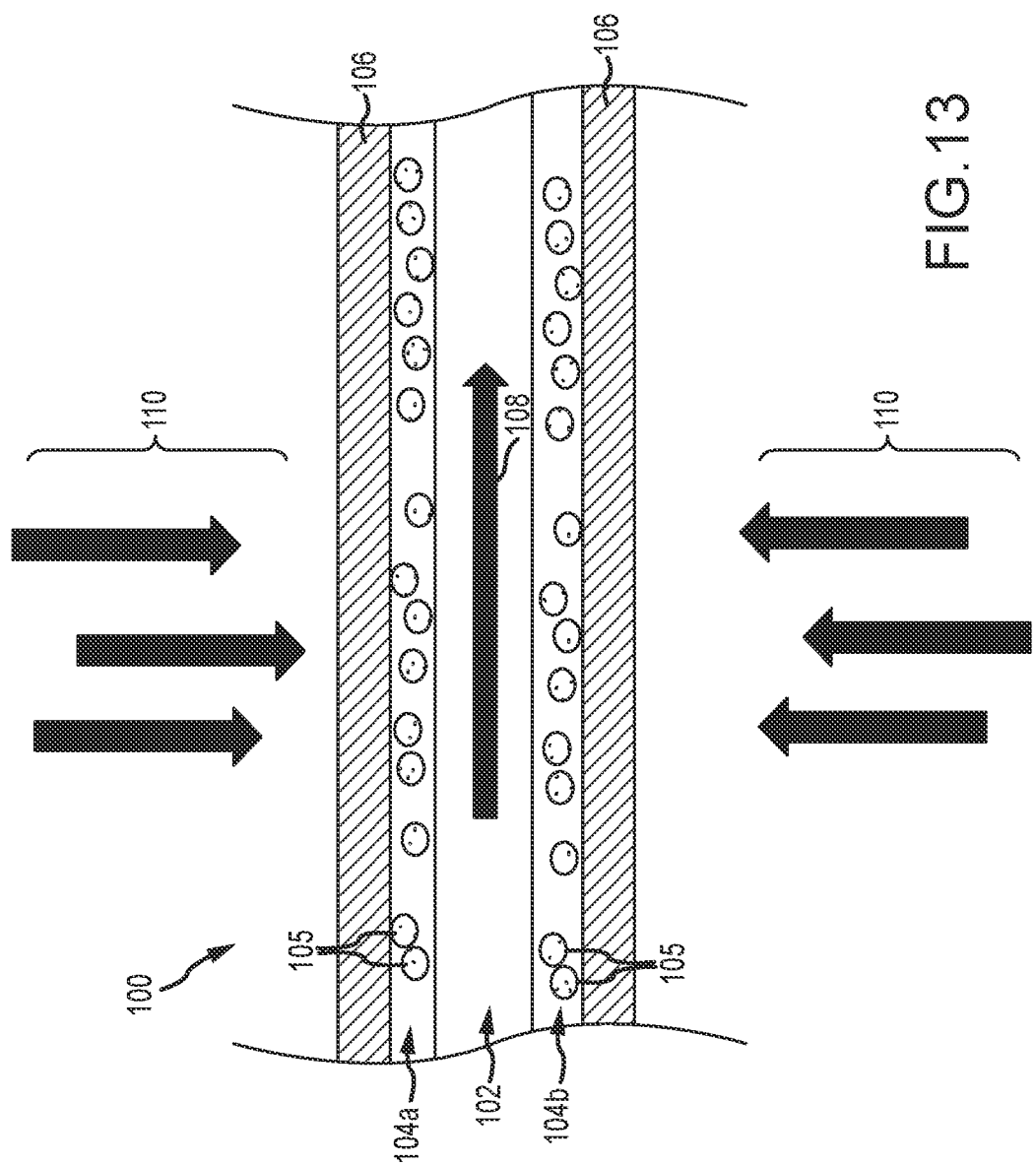
FIG. 13 is a cross-sectional elevation view of an implantable encapsulation device and related methods according to embodiments of the present disclosure.
Figure 14:
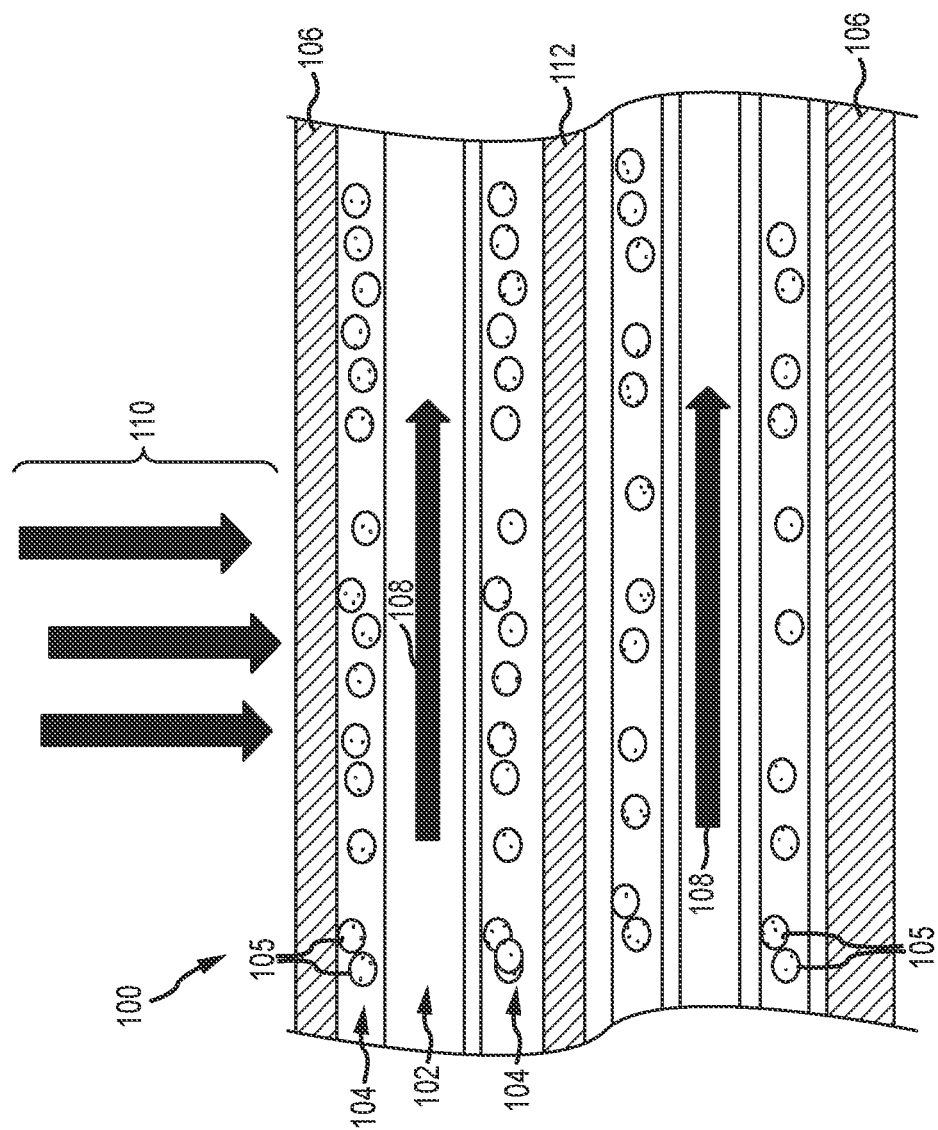
FIG. 14 is a cross-sectional elevation view of an implantable encapsulation device and related methods according to embodiments of the present disclosure.

FIGS. 13 and 14 illustrate embodiments according to the present disclosure relating to use of an encapsulation device in which a channel for delivery of a fluid is used to freeze and/or thaw (i.e., modulate the temperature of) cells in the device. Use of the device as described herein may more rapidly and effectively freeze (i.e., cryopreserve) cells, for example, after loading the device with cells and before implantation. Likewise, cells may be more rapidly and effectively warmed prior to implantation. In this manner, there is less opportunity for damage to cells to occur.

FIG. 13 is a cross-sectional elevation view of an encapsulation device 100 according to embodiments of the present disclosure. The encapsulation device 100 includes a flow channel 102 extending through or at least partially through an interior volume of the device 100. The channel 102 extends between two cell chambers 104a, 104b and the device may optionally include an outer immunoisolation membrane and/or vascularization membrane 106. As shown in FIG. 13, a fluid flow 108 is contemplated as being provided through the channel 102. During a freezing or cryopreservation step, the flow 108 is contemplated as being a flow of fluid (e.g. a cryopreservation fluid such as a liquid including dimethyl sulfoxide, or the like) at a temperature below 0° Celsius to cool or freeze the device and cells 105 provided within the cell chambers 104a, 104b. Alternatively, the flow 108 is contemplated as including chilled air or various other fluids. A second flow of fluid 110 is provided to an exterior of the device. The second flow is contemplated as including a cryopreservation medium and/or a washing medium. In this manner utilizing the fluid channel 102 for cooling, cells in the cell chambers 104a, 104b may be more rapidly and efficiently cooled and frozen because cooling medium from fluid flows 108 and 110 comes into contact with two sides of the cell chambers 104a, 104b.

Additionally, it is contemplated that at least one of the fluid flows 108, 110 is provided as a warming or thawing process that includes a fluid with a temperature above 0° Celsius for warming or thawing the device 100 and housed cells prior to implantation. The channel 102 is further operable to be provided as and function as a conduit for delivering gas (e.g. oxygen) or nutrients to cells prior to or subsequent to implantation.

FIG. 14 is a cross-sectional elevation view of an encapsulation device 100 according to embodiments of the present disclosure. As shown, a stacked arrangement is provided wherein the encapsulation device 100 includes a plurality of channels 102, and a plurality of cell chambers 104. Fluid flow 108 as described herein is contemplated as being provided through the channels 102. The channel 102 of FIG. 14 may include separate channels. Alternatively, the channel 102 may include a single circuitous channel that extends through an interior of the encapsulation device 100. Vasculature 106, 112 is shown relative to the cell chambers 104. The channels 102 are contemplated as being provided with fluid flow 108 for cryopreservation, thawing (or heating) and oxygen and nutrient delivery to the cells.

The systems and methods of FIGS. 4-6 of matrix and scaffold formation may be used with the embodiments of FIGS. 7-14. It will be recognized, however, that the embodiments of FIGS. 7-14 are not limited to the concepts and methods of matrix formation of FIGS. 4-6 (for example). Indeed, it is believed that patentable features and various novel, useful features are provided in the embodiments of FIGS. 7-14 irrespective of the method of formation, cross-linking of matrices, etc. Similarly, it is believed that patentable features and various novel, useful features are provided in the embodiments of FIGS. 1-6 regardless of the orientation, shape, and layout of the gas channel(s).

FIGS. 15-19 show embodiments according to the present disclosure relating to a stacked or multi-stack, oxygen-enabled encapsulation device 120 with enhanced vascularization and/or ability for temperature modulation. Use of the device is described herein may enable an increase in viability by reducing oxygen consumption rates and toxic metabolite production rates by an implanted cell.

A stacked arrangement is provided where an encapsulation device 120 includes a plurality of cell chambers 122 with voids 123 operable to receive and house cells 124 within a formed matrix. The cells 124 may be provided in the form of spheroids including multiple cells within each spheroid. Alternatively, individual cells or "clumps" of cells may be loaded into the cell chambers 122 of the device 120. In some embodiments, the chambers 122 or other membranes of the encapsulation device 120 may be constructed from materials such as polytetraflouroethylene (PTFE) or other similar material (e.g., as described throughout the present disclosure). It is noted embodiments related to the formation of a matrix within a void for embedding or aggregating cells in a graduated matrix by use of a fluid channel and a void for housing of cells as described with respect to FIGS. 4-6 may be applied to the embodiments shown in FIGS. 15-19 without departing from the scope of the present disclosure.

The encapsulation device 120 includes one or more channels 126. The channels 126 extend through or at least partially through an interior volume of the encapsulation device 120. In one example embodiment, a channel 126 may be provided adjacent to and extends between two cell chambers 122a, 122b. The channels 126 are fabricated from a rubber or plastic. For example, the channels 126 may be fabricated from a fluid-permeable silicone rubber tube, or may be fabricated from another material as described throughout the present disclosure. The channels 126 include one or more ports 128 which operate as inlets/outlets for a fluid. For example, the encapsulation device 120 may include an inlet 128a and an outlet 128b for oxygen.

The encapsulation device 120 may include one or more immunoisolation membranes 130 and/or one or more vascularization membranes 132.

In one example embodiment as shown in FIG. 15, an immunoisolation membrane 130a may at least partially surround or encapsulate the cell chamber 122a and a vascularization membrane 132a may at least partially surround or encapsulate the immunoisolation membrane 130a. An immunoisolation membrane 130b may at least partially surround or encapsulate the cell chamber 122b and a vascularization membrane 132b may at least partially surround or encapsulate the immunoisolation membrane 130b. For instance, both the vascularization membrane 132a may be positioned on at least a side of the cell chamber 122a and the vascularization membrane 132b may be positioned on at least a side of the cell chamber 122b adjacent to the channel 126.

Figure 19:
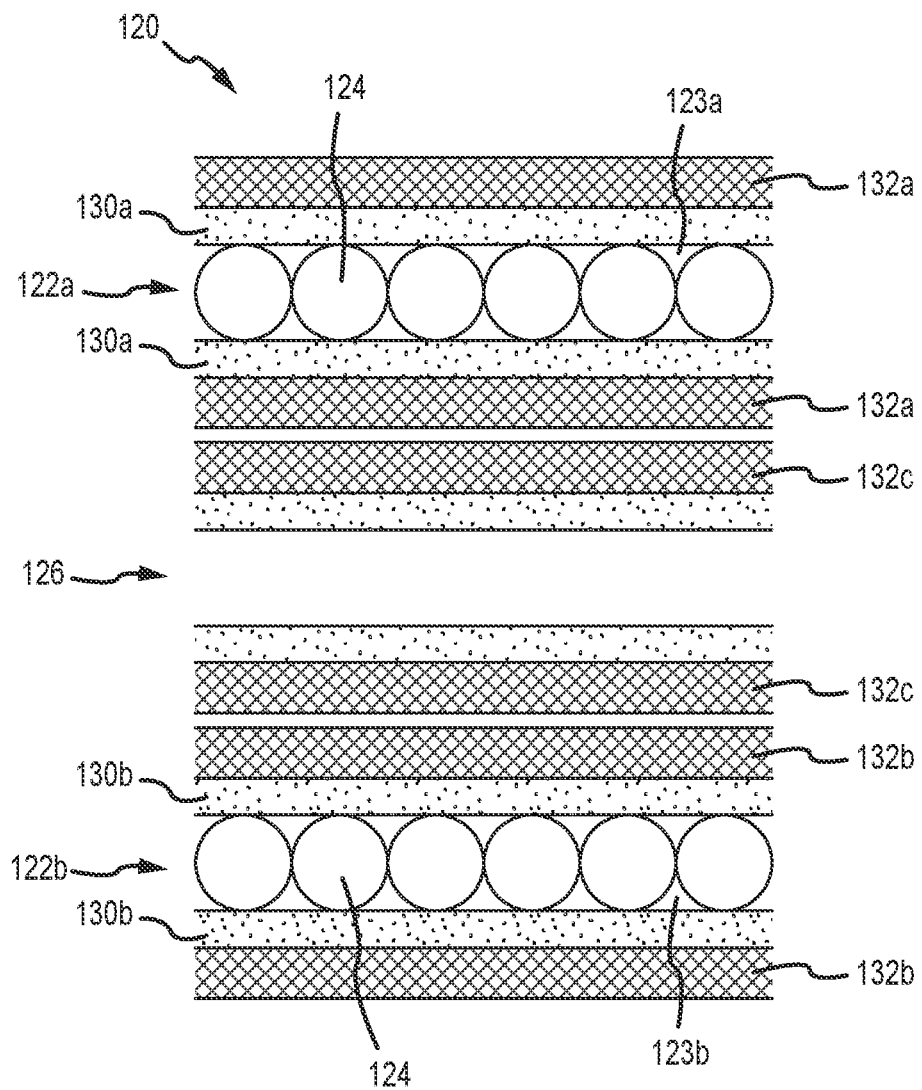
FIG. 19 is a cross-sectional elevation view of an implantable encapsulation device and related methods according to embodiments of the present disclosure.

In another example embodiment as shown in FIG. 19, a vascularization membrane 132c may at least partially surround and encapsulate the channel 126 in addition to the arrangement as provided in the example embodiment described with respect to FIG. 15 of one or more outer immunoisolation membranes 130 and/or one or more vascularization membranes 132a, 132b respective to the cell chambers 122a, 122b. Including a vascularization membrane 132c around the channel 126 may allow for vascularization formation around the channel 126 in addition to vascularization formation about the cell chambers 122a, 122b. The channel 126 may range between 0.20 millimeters (mm) (1/128th inches) and 0.80 mm (1/32nd inches) in diameter (d).

The encapsulation device 120 is secured with space provided to permit vascularization. For example, the encapsulation device 120 may be secured by sutures, a kinetic glue, or welded together (e.g., spot welded, or the like). In some embodiments, including those shown in FIGS. 15 and 17, a plurality of spot welds 134 are provided to join or attach features of the encapsulation device 120.

As shown in a cross-sectional top plan view in FIG. 17 of the encapsulation device 120, the cell chambers 122a, 122b are stacked such that cell chamber 122a is above the cell chamber 122b (or below, depending on view) and similarly oriented. The one or more channels 126 may make a single pass through the encapsulation device 120, or may be wound at least once. For example, the one or more channels 126 may be wound once or multiple times while embedded between vascularization membranes 132. For instance, the one or more channels 126 may be embedded between vascularization membranes 132a, 132b and/or within vascularization membrane 132c as shown throughout FIGS. 15-19.

In this regard, the encapsulation device 120 embodied in at least FIGS. 15-19 include a two cell chambers 122a, 122b separated by a central flow channel 126 or chamber for oxygen delivery, which allow for vasculature to be created between the two stacked cell chambers 122a, 122b and promote oxygen delivery through the gas-permeable flow channel 126. With this configuration, fluid may permeate from the channel 126 and into the cell chambers 122a, 122b through the respective vascularization membranes 132a, 132b. For example, oxygen is allowed to diffuse through the vascularization membranes 132a, 132b and infiltrate at least a portion of the respective cell chambers 122a, 122b.

FIGS. 20-34 show embodiments according to the present disclosure relating to a stacked or multi-stack, oxygen-enabled encapsulation device 140 with enhanced vascularization and/or ability for temperature modulation. The enhanced vascularization and/or temperature modulation may occur in vitro or in vivo.

A stacked arrangement is provided where an encapsulation device 140 includes a plurality of cell chambers 142 with voids 143 operable to receive and house cells 144 within a formed matrix. The cells 144 may be provided in the form of spheroids including multiple cells within each spheroid. Alternatively, individual cells or "clumps" of cells may be loaded into the cell chambers 142 of the device 140.s In some embodiments, the chambers 142 or membranes are constructed from materials such as polytetraflouroethylene (PTFE) or other similar material (e.g., as described throughout the present disclosure). It is noted embodiments related to the formation of a matrix within a void for embedding or aggregating cells in a graduated matrix by use of a fluid channel and a void for housing of cells as described with respect to FIGS. 4-6 may be applied to the embodiments shown in FIGS. 20-34 without departing from the scope of the present disclosure.

The encapsulation device 140 includes one or more channels 146. The channels 146 extend through or at least partially through an interior volume of the encapsulation device 140. In one example embodiment, a channel 146a is provided adjacent to and extends between two cell chambers 142a, 142b, and a channel 146b is provided adjacent to and extends between two cell chambers 142b, 142c. The channels 146 are fabricated from a rubber or plastic. For example, the channels 146 may be fabricated from a fluid-permeable silicone rubber tube, or may be fabricated from another material as described throughout the present disclosure.

Figure 20:
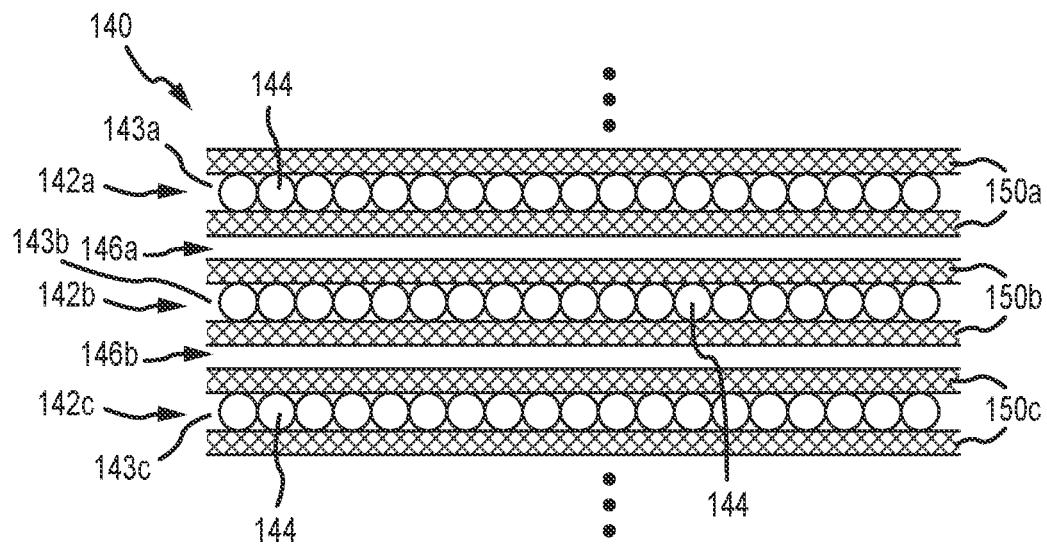
FIG. 20 is a cross-section elevation view of an implantable encapsulation device and related methods according to embodiments of the present disclosure.
Figure 21:
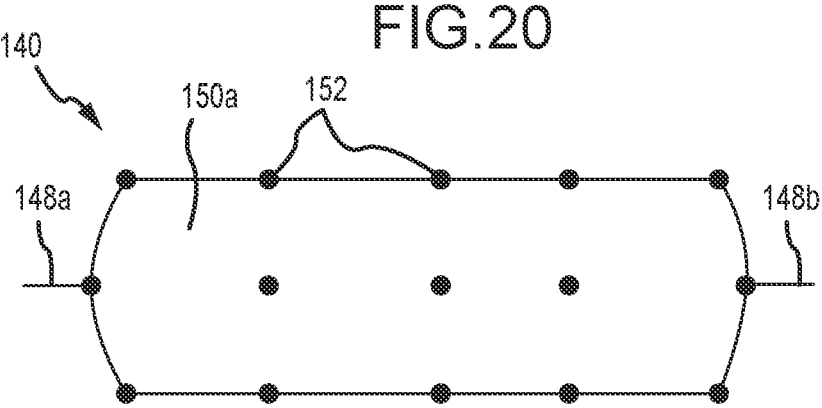
FIG. 21 is a top plan view of an implantable encapsulation device and related methods according to embodiments of the present disclosure.
Figure 22:
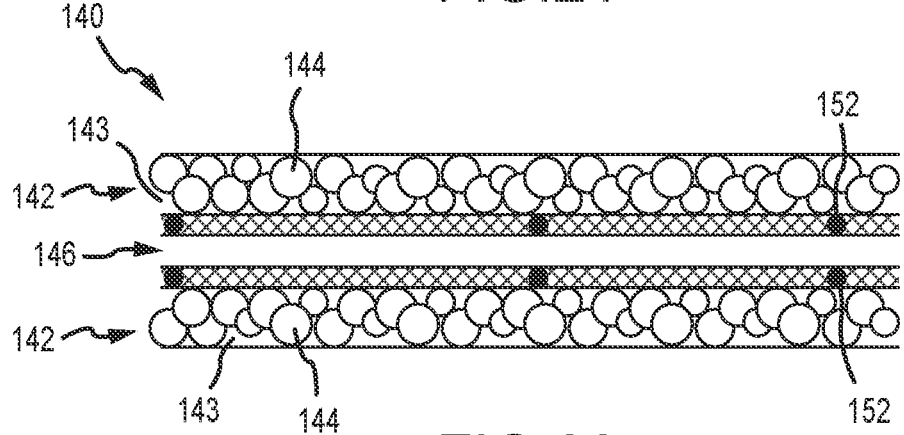
FIG. 22 is a cross-sectional elevation view of an implantable encapsulation device and related methods according to embodiments of the present disclosure.

It is noted the encapsulation device 140 is not limited to the three chambers 142 and two channels 146 as illustrated in FIG. 20. Instead, the encapsulation device 140 may include any number of chambers 142 and channels 146 in a stacked configuration, as represented by the sets of three dots in FIG. 20, without departing from the scope of the present disclosure.

The channels 146 include one or more ports 148 which operate as inlets/outlets for a fluid. For example, the encapsulation device 140 may include an inlet 148a and an outlet 148b for oxygen. For instance, the inlet 148a and the outlet 148b may be separate.

Figure 24:
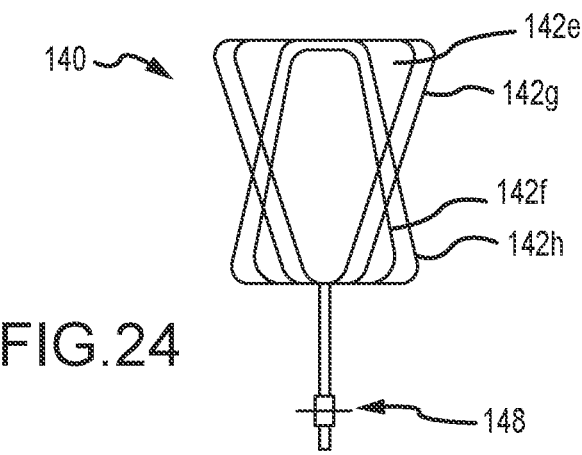
FIG. 24 is a transparent top plan view of an implantable encapsulation device and related methods according to embodiments of the present disclosure.
Figure 25:
FIG. 25 is a front elevation view of an implantable encapsulation device and related methods according to embodiments of the present disclosure.
Figure 26:
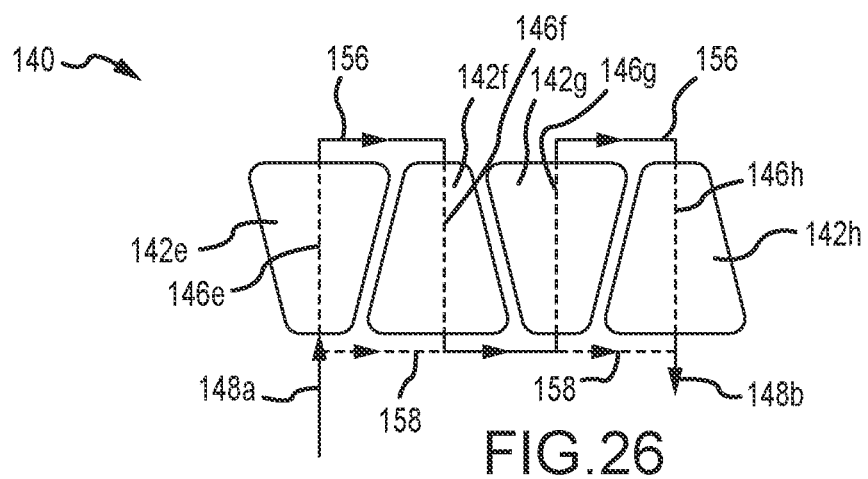
FIG. 26 is an exploded top plan view of an implantable encapsulation device and related methods according to embodiments of the present disclosure.

As shown in an example embodiment in FIGS. 24-26, the inlet 148a and the outlet 148b may be combined as a multi-layer or sheathed port (e.g., a skin integrated catheter) embedded within a stack of chambers 142e, 142f, 142g, 142h with respective channels 146e, 146f, 146g, 146h, where the inlet 148a is in an inner portion and the outlet 148b is in an outer portion (or vice versa). FIG. 26 provides an exploded view of the stack in FIG. 24, where channels 146 within adjacent chambers 142 in the stack are connected by an exterior channel or line 156 to complete a circuit between the inlet 148a and the outlet 148b. In addition, a direct exterior channel or line 158 as shown in FIG. 26 may supplement or bypass at least a portion of the pathway created by the channels 146 and the exterior channels or lines 156 to couple the inlet 148a to the outlet 148b directly. It is noted the exterior channels 156, 158 may be coated with vasculature or vascularization membranes.

Although embodiments of the present disclosure are directed to the channels 146 being used for gas delivery, it is noted herein the channels 146 may in addition or alternatively be used as a heat exchanger.

The encapsulation device 140 may include one or more vascularization membranes 150. In one example embodiment as shown in FIG. 20, a vascularization membrane 150a may at least partially surround or encapsulate the cell chamber 142a, a vascularization membrane 150b may at least partially surround or encapsulate the cell chamber 142b, and a vascularization membrane 150c may at least partially surround or encapsulate the cell chamber 142c. For instance, both the vascularization membrane 150a may be positioned on at least a side of the cell chamber 142a and the vascularization membrane 150b may be positioned on at least a side of the cell chamber 142b adjacent to the channel 146a. Both the vascularization membrane 150b may be positioned on at least a side of the cell chamber 142b and the vascularization membrane 150c may be positioned on at least a side of the cell chamber 124c adjacent to the channel 146b.

The encapsulation device 140 is secured with space provided to permit vascularization. For example, the encapsulation device 140 may be secured by sutures, a kinetic glue, or welded together (e.g., spot welded, or the like). In some embodiments, including those shown in FIGS. 21, 22, and 29, a plurality of spot welds 152 are provided to join or attach features of the encapsulation device 140.

As shown in the views in FIGS. 27, 28, 31, 32, and 34 of the encapsulation device 140, the cell chambers 142 are stacked. The one or more channels 146 may make a single pass through the encapsulation device 140, or may be wound at least once. For example, the one or more channels 146 may be wound once or multiple times, embedded between vascularization membranes 150. For instance, where there are chambers 142a, 142b, 142c, the one or more channels 146 may be embedded between vascularization membranes 150a, 150b and/or between vascularization membrane 150b, 150c as shown throughout FIGS. 20-34. It is noted herein, however, the encapsulation device 140 may include a separate vascularization membrane in which the channels 146 are embedded, where the separate vascularization membranes are spaced from the vascularization membranes 150a, 150b, 150c a select amount to allow for vascularization in the space between the cell chambers 142 and the channels 146. In this regard, vasculature may form between the channels 146 (or gas chambers 146) and the cell chambers 142. It is noted where the channel 146 is wound or where there are multiple channels 146, spacing between channel passes or channels may range between 50 and 500 micrometers.

Figure 23:
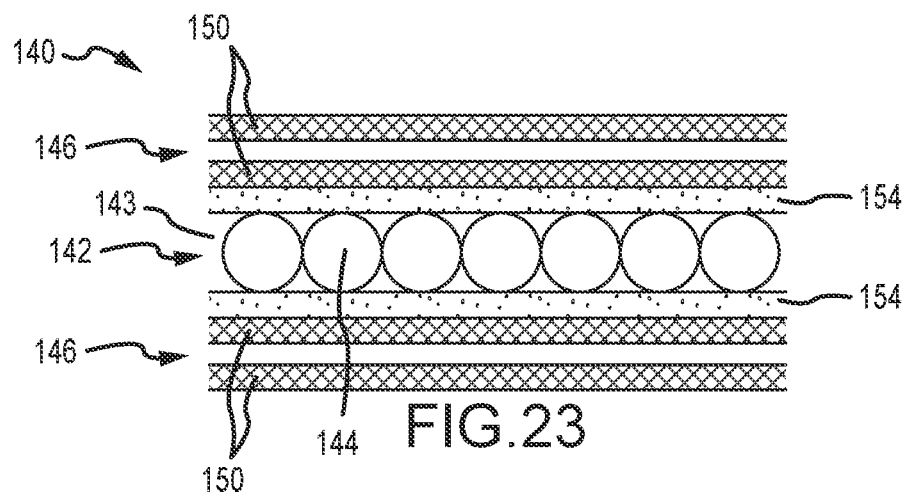
FIG. 23 is a cross-sectional elevation view of an implantable encapsulation device and related methods according to embodiments of the present disclosure.

As shown in FIGS. 23 and 30, the encapsulation device 140 may additionally include immunoisolation membranes 154. In one example embodiment, an immunoisolation membrane 154 may at least partially surround or encapsulate the cell chamber 142 and a vascularization membrane 150 may at least partially surround or encapsulate the immunoisolation membrane 154. It is contemplated any of the embodiments shown in FIGS. 20-34 may include both the vascularization membranes 150 and the immunoisolation membranes 154, although not shown.

FIG. 30 is a cross-sectional elevation view of a device with a channel 146 extending therein. The channel is contemplated as comprising a support member 143 to support and position the channel. The channel 146 is contemplated as comprising a serpentine or winding channel (see, e.g., FIG. 28). The support member 143 is contemplated as comprising a mesh or porous structure to allow cells and other features to pass through and extend above and below the channel 146. The support member 143 is contemplated as comprising pores with a pore size ranging between 1 and 750 micrometers. For example, the pore size may range between 150 and 300 micrometers. By way of another example, the pore size may be at least 400 micrometers. One of skill in the art will recognize that the pore sizes of the support member 143 may vary based on a particular application, and no limitation with respect to pore size is provided.

It is noted the entire encapsulation device 140 may be secured via spot welds, gluing or the like. In addition, it is noted the tubing 146 may be secured on the bottom or top chamber 142 (e.g., of the stack) vascularization membrane 150 (e.g., that is not isolating) or immunoisolation membrane 154.

Figure 31:
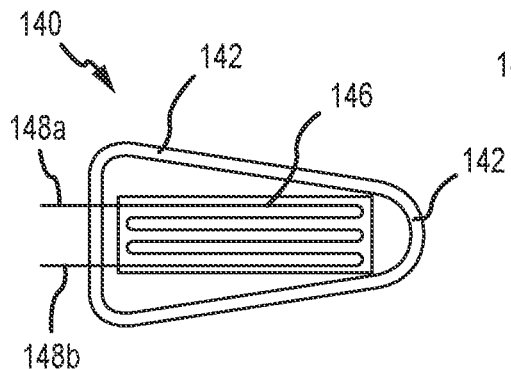
FIG. 31 is a cross-sectional top plan view of an implantable encapsulation device and related methods according to embodiments of the present disclosure.
Figure 32:
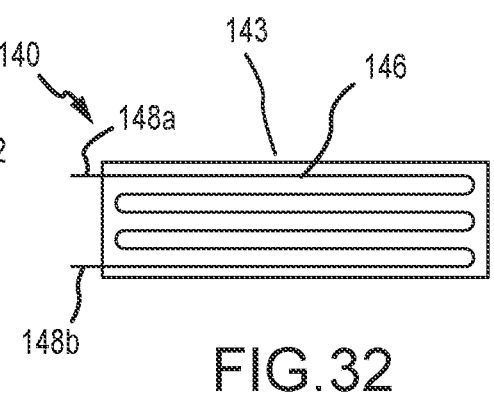
FIG. 32 is a cross-sectional top plan view of portions of an implantable encapsulation device and related methods according to embodiments of the present disclosure.
Figure 33:
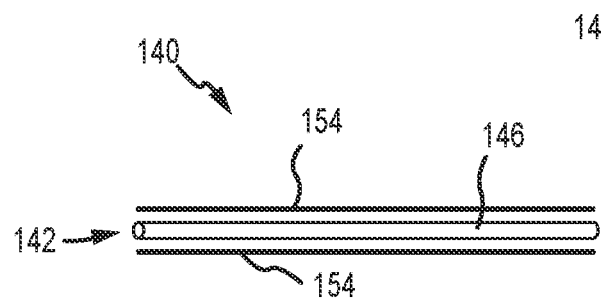
FIG. 33 is a cross-sectional elevation view of portions of an implantable encapsulation device and related methods according to embodiments of the present disclosure.
Figure 34:
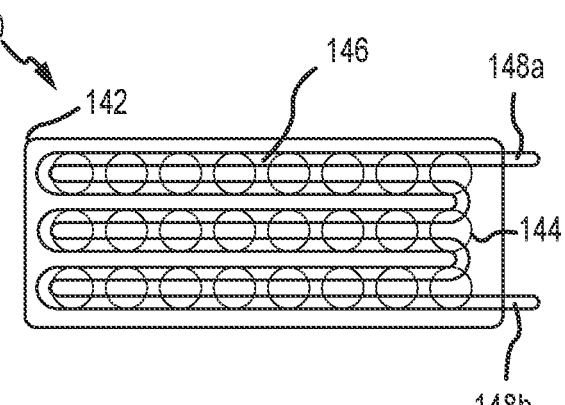
FIG. 34 is a transparent top plan view of portions of an implantable encapsulation device and related methods according to embodiments of the present disclosure.

FIGS. 31-32 depict a support member 143. The support member 143 is contemplated as an optional support structure for a channel 146, for example. In various embodiments, the support member comprises a mesh or permeable member that is provided within or at least partially within the encapsulation device 140. A vascularization membrane is contemplated as being provided on one or more sides of the support member.

In this regard, the encapsulation device 140 embodied in at least FIGS. 20-34 include two or more cell chambers 142 separated or partially separated by one or more flow channels 146 for oxygen delivery, which allow for vasculature to be created between the stacked cell chambers 142 and promote oxygen delivery through the channels 146, while also providing support via the vasculature for when the oxygen delivery is interrupted. With this configuration, fluid may permeate from the one or more channels 146 and into the cell chambers 146 through the respective vascularization membranes 150. For example, oxygen is allowed to diffuse through the vascularization membranes 150 and infiltrate at least a portion of the respective cell chambers 142. Pumping a "cold" gas or other liquid through the chambers 146 and/or channels 146 may enable an increase in viability by reducing implanted cell oxygen consumption, and may also reduce toxic metabolite production rates. For example, a "cold" gas may be between 0 degrees Celsius (° Celsius or ° C.) and 37° Celsius. For instance, the "cold" gas may be between 17° Celsius and 27° Celsius, and preferably may be 17° Celsius. In addition, the "cold" gas may be at 8° Celsius room temperature (RT).

It is noted that for purposes of the present disclosure, "oxygen" may refer to a pure or substantially pure $O_2$ gas, a mixture of pure $O_2$ gas and air, or air. In addition, it is noted any embodiment directed to a particular encapsulation device as shown in FIGS. 1-34 may be directed to any other encapsulation device shown without departing from the scope of the present disclosure, unless otherwise noted.

Although various methods and systems of the present disclosure contemplate the provision of cells within a matrix provided within an encapsulation device, methods and systems are contemplated that do not include a matrix as shown and described herein. For example, in some embodiments, spheroid cells are provided in a cell chamber and a matrix is not formed in the encapsulation device. Methods of the present disclosure, including but not limited to those related to cryopreservation are contemplated for such devices including spheroids. Examples of spheroid cells are provided in International Application PCT/NL2017/050098 to Van Beurden which is hereby incorporated by reference in its entirety.

The examples set forth above are provided to give those of ordinary skill in the art a complete disclosure and description of how to make and use the embodiments of the methods for prediction of the selected modifications that may be made to a biomolecule of interest, and are not intended to limit the scope of what the inventors regard as the scope of the disclosure. Modifications of the above-described modes for carrying out the disclosure may be used by persons of skill in the art, and are intended to be within the scope of the following claims.

It is to be understood that the disclosure is not limited to particular methods or systems, which can, of course, vary. It is also to be understood that the terminology used herein is for the purpose of describing particular embodiments only, and is not intended to be limiting.

A number of embodiments of the disclosure have been described. Nevertheless, it will be understood that various modifications may be made without departing from the spirit and scope of the present disclosure. Accordingly, other embodiments are within the scope of the following claims.

What is claimed is:

1. An implantable encapsulation device, comprising:
a first void for receiving and encapsulating cells, wherein the first void has a first side;
a channel adjacent the first side of the first void and separated from the first void by a gas permeable membrane;
wherein the channel occupies a portion of the first side of the first void that is less than all of the first side of the first void;
wherein a portion of the first side of the first void not occupied by the channel comprises a vascularization membrane;
a second void having a first side adjacent the channel and separated from the second void by a gas permeable membrane and opposite the first void;
wherein the channel occupies a portion of the first side of the second void that is less than all of the first side of the second void;
wherein a portion of the first side of the second void not occupied by the channel comprises a vascularization membrane; and
wherein a portion of the channel is surrounded by a channel vascularization membrane positioned between the channel and at least one of the vascularization membrane of the first void or the vascularization membrane of the second void, and wherein the channel vascularization membrane is separated by a spacing between at least one of the vascularization membrane of the first void or the vascularization membrane of the second void to allow for vascularization in the spacing.

2. The implantable encapsulation device of claim 1, wherein the first void has a second side and the second side comprises an immuno-isolation membrane and a vascularization membrane.

3. The implantable encapsulation device of claim 1, wherein the channel forms a serpentine path on the first side of the first void.

4. The implantable encapsulation device of claim 1, wherein the channel forms a straight path on the first side of the first void.

5. The implantable encapsulation device of claim 1, wherein the channel occupies between 10% and 90% of the area of the first side of the first void.

6. The implantable encapsulation device of claim 1, wherein the first void comprises a cell-housing chamber comprising a matrix gradient having higher cross-linking near the channel and a lower cross-linking density near the vascularization membrane.

7. The implantable encapsulation device of claim 1, wherein the channel comprises a gas permeable channel operable to selectively deliver oxygen to at least the vascularization membrane.

8. The implantable encapsulation device of claim 1, wherein the channel is operable to receive and transmit a flow of cryopreservation fluid to cool or freeze cells provided within at least one of the first void and the second void.

9. The implantable encapsulation device of claim 8, wherein the cryopreservation fluid comprises dimethyl sulfoxide.

10. An implantable encapsulation device, comprising:
a first void for receiving and encapsulating cells, wherein the first void has a first side;
a channel adjacent the first side of the first void and separated from the first void by a gas permeable membrane;
wherein the channel occupies a portion of the first side of the first void that is less than all of the first side of the first void;
wherein a portion of the first side of the first void not occupied by the channel comprises a vascularization membrane; and
wherein the first void comprises a cell-housing chamber comprising a matrix gradient having higher cross-linking near the channel and a lower cross-linking density near the vascularization membrane.

11. The implantable encapsulation device of claim 10, wherein the channel is operable to receive and transmit a flow of cryopreservation fluid to cool or freeze cells provided within the first void.

12. The implantable encapsulation device of claim 11, wherein the cryopreservation fluid comprises dimethyl sulfoxide.

* * * * *